US012648994B2

(12) United States Patent
Illei et al.

(10) Patent No.: US 12,648,994 B2
(45) Date of Patent: Jun. 9, 2026

(54) METHODS OF TREATING IMMUNE-MEDIATED PULMONARY INJURY WITH AN ANTI-ILT7 ANTIBODY

(71) Applicant: Viela Bio, Inc., Deerfield, IL (US)

(72) Inventors: Gabor Illei, Deerfield, IL (US); William Rees, Deerfield, IL (US); Jorn Drappa, Deerfield, IL (US)

(73) Assignee: Viela Bio, Inc., Deerfield, IL (US)

( * ) Notice: Subject to any disclaimer, the term of this patent is extended or adjusted under 35 U.S.C. 154(b) by 809 days.

(21) Appl. No.: 17/937,073

(22) Filed: Sep. 30, 2022

(65) Prior Publication Data

US 2023/0151093 A1     May 18, 2023

Related U.S. Application Data

(63) Continuation of application No. PCT/US2021/025600, filed on Apr. 2, 2021.

(60) Provisional application No. 63/066,955, filed on Aug. 18, 2020, provisional application No. 63/052,596, filed on Jul. 16, 2020, provisional application No. 63/004,866, filed on Apr. 3, 2020.

(51) Int. Cl.
| | |
|---|---|
| *A61P 11/00* | (2006.01) |
| *A61K 39/395* | (2006.01) |
| *A61P 31/14* | (2006.01) |
| *A61P 31/20* | (2006.01) |
| *A61P 37/06* | (2006.01) |
| *A61K 39/00* | (2006.01) |
| *C07K 14/705* | (2006.01) |
| *C07K 16/28* | (2006.01) |

(52) U.S. Cl.
CPC .......... *A61K 39/3955* (2013.01); *A61P 11/00* (2018.01); *A61P 31/14* (2018.01); *A61P 31/20* (2018.01); *A61P 37/06* (2018.01); *A61K 2039/505* (2013.01); *A61K 2039/54* (2013.01); *A61K 2039/545* (2013.01); *C07K 14/70503* (2013.01); *C07K 16/2803* (2013.01); *C07K 2317/21* (2013.01); *C07K 2317/41* (2013.01)

(58) Field of Classification Search
CPC ...... A61K 39/3955; A61P 11/00; A61P 31/14; A61P 31/20; A61P 37/06; C07K 14/70503; C07K 16/2803
See application file for complete search history.

(56) References Cited

U.S. PATENT DOCUMENTS

| | | | |
|---|---|---|---|
| 4,683,195 A | 7/1987 | Mullis et al. |
| 4,741,900 A | 5/1988 | Alvarez et al. |
| 4,873,192 A | 10/1989 | Kunkel |
| 4,885,166 A | 12/1989 | Meyer et al. |
| 4,902,618 A | 2/1990 | Berg |
| 5,116,964 A | 5/1992 | Capon et al. |
| 5,122,464 A | 6/1992 | Wilson et al. |
| 5,223,409 A | 6/1993 | Ladner et al. |
| 5,225,538 A | 7/1993 | Capon et al. |
| 5,225,539 A | 7/1993 | Winter |
| 5,314,995 A | 5/1994 | Fell, Jr. et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,693,761 A | 12/1997 | Queen et al. |
| 5,693,762 A | 12/1997 | Queen et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,859,205 A | 1/1999 | Adair et al. |
| 5,885,793 A | 3/1999 | Griffiths et al. |
| 5,892,019 A | 4/1999 | Schlom et al. |
| 5,939,598 A | 8/1999 | Kucherlapati et al. |
| 5,969,108 A | 10/1999 | McCafferty et al. |
| 6,172,197 B1 | 1/2001 | McCafferty et al. |
| 6,180,370 B1 | 1/2001 | Queen et al. |
| 6,300,064 B1 | 10/2001 | Knappik et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |

(Continued)

FOREIGN PATENT DOCUMENTS

| | | |
|---|---|---|
| AU | 2006328470 A | 6/2007 |
| AU | 2012244391 A1 | 11/2012 |

(Continued)

OTHER PUBLICATIONS

Cao et al, 2010. Immunol Rev. 234(1), 22 pages as printed.*
Benjamini et al, 1991. Immunology: A Short Course, 2nd edition, p. 40 only.*
Ferrara et al (2015. mAbs. 7(1): 32-41).*
Accession NP_036408, 2003, pp. 1-2.
Niewold T., et al., "Targeting type I interferon in systemic lupus erythematosus" , Annals of the Rheumatic Diseases, vol. 12, May 26, 2016 (May 26, 2016), pp. 377-378.
Viela B., "NCT03817424 A Study to Evaluate VIB7734 in Participants With Systemic Lupus Erythematosus (SLE), Cutaneous Lupus Erythematosus (CLE), Sjogren's Syndrome, Systemic Sclerosis, Polymyositis, and Dermatomyositis", Clinicaltrials.gov, Jan. 22, 2019 (Jan. 22, 2019), Retrieved from the Internet: URL:https://clinicaltrials.gov/study/NCT03817424?term=NCT03817424&rank=1&tab=table [retrieved on Nov. 21, 2023], 9 pages.

(Continued)

*Primary Examiner* — Zachary C Howard
(74) *Attorney, Agent, or Firm* — Bilyana Georgieva

(57) ABSTRACT

The present disclosure relates to methods for treating or preventing immune-mediated pulmonary injury (IMPI) in a subject in need thereof, the method comprising administering to the subject an anti-Type I interferon (anti-T1i) therapy that blocks the activity, function or production of Type I interferon (T1i) in the subject, wherein the anti-T1i therapy is administered to the subject infected with a respiratory virus that causes a delayed T1i response in the subject.

27 Claims, 12 Drawing Sheets

Specification includes a Sequence Listing.

(56) References Cited

U.S. PATENT DOCUMENTS

| | | | |
|---|---|---|---|
| 6,593,081 B1 | 7/2003 | Griffiths et al. |
| 6,653,068 B2 | 11/2003 | Frisch et al. |
| 6,706,484 B1 | 3/2004 | Knappik et al. |
| 6,737,056 B1 | 5/2004 | Presta |
| 7,087,726 B2 | 8/2006 | Chuntharapai et al. |
| 7,264,963 B1 | 9/2007 | Knappik et al. |
| 7,619,070 B2 | 11/2009 | Cardarelli et al. |
| 7,662,381 B2 | 2/2010 | Cardarelli et al. |
| 7,741,449 B2 | 6/2010 | Witte et al. |
| 7,888,484 B2 | 2/2011 | Cardarelli et al. |
| 8,071,323 B2 | 12/2011 | Dimitrov et al. |
| 8,084,585 B2 | 12/2011 | Kamogawa et al. |
| 8,470,992 B2 | 6/2013 | Kamogawa et al. |
| 8,605,807 B1 | 12/2013 | Macrae |
| 8,758,757 B2 | 6/2014 | Cardarelli et al. |
| 8,901,036 B2 | 12/2014 | Willms et al. |
| 8,912,624 B2 | 12/2014 | Kakehata |
| 9,114,438 B2 | 8/2015 | Hoinkis et al. |
| 9,208,495 B2 | 12/2015 | Altberg et al. |
| 11,072,652 B2 | 7/2021 | Vousden et al. |
| 11,673,950 B2 | 6/2023 | Vousden et al. |
| 2002/0123057 A1 | 9/2002 | Zauderer et al. |
| 2002/0146825 A1 | 10/2002 | Uhler |
| 2003/0148316 A1 | 8/2003 | Lipford et al. |
| 2004/0132101 A1 | 7/2004 | Lazar et al. |
| 2007/0025992 A1 | 2/2007 | Takayama et al. |
| 2008/0050340 A1 | 2/2008 | Kedl et al. |
| 2009/0280128 A1 | 11/2009 | Kamogawa et al. |
| 2010/0070346 A1 | 3/2010 | Davis |
| 2011/0311558 A1 | 12/2011 | Cao et al. |
| 2012/0135003 A1 | 5/2012 | Kamogawa et al. |
| 2012/0316071 A1 | 12/2012 | Smider et al. |
| 2013/0259872 A1 | 10/2013 | Kamogawa et al. |
| 2013/0344509 A1 | 12/2013 | Nakamura et al. |
| 2014/0056889 A1 | 2/2014 | Morimoto et al. |
| 2015/0133317 A1 | 5/2015 | Robinson et al. |
| 2016/0060326 A1 | 3/2016 | Zhou et al. |
| 2016/0130343 A1 | 5/2016 | Kamogawa et al. |
| 2017/0204179 A1 | 7/2017 | Kamogawa et al. |
| 2020/0339673 A1 | 10/2020 | Vousden et al. |
| 2020/0339682 A1 | 10/2020 | Kamogawa et al. |
| 2022/0144940 A1 | 5/2022 | Vousden et al. |
| 2022/0403020 A1 | 12/2022 | Rees et al. |
| 2023/0250167 A1 | 8/2023 | Vousden et al. |
| 2024/0287176 A1 | 8/2024 | Drappa |

FOREIGN PATENT DOCUMENTS

| | | | |
|---|---|---|---|
| CA | 3017197 A1 | 9/2017 |
| CN | 1461310 A | 12/2003 |
| CN | 104284903 A | 1/2015 |
| CN | 104884049 A | 9/2015 |
| CN | 105111311 A | 12/2015 |
| CN | 109414499 A | 5/2022 |
| EP | 0119476 A2 | 9/1984 |
| EP | 0396387 A2 | 11/1990 |
| EP | 1964852 A1 | 9/2008 |
| JP | 2019516392 A | 6/2019 |
| KR | 20140053232 A | 5/2014 |
| RU | 2431638 C2 | 10/2011 |
| WO | WO-8403105 A1 | 8/1984 |
| WO | WO-9002809 A1 | 3/1990 |
| WO | WO-9110737 A1 | 7/1991 |
| WO | WO-9201047 A1 | 1/1992 |
| WO | WO-9218619 A1 | 10/1992 |
| WO | WO-9311236 A1 | 6/1993 |
| WO | WO-9515982 A2 | 6/1995 |
| WO | WO-9520401 A1 | 8/1995 |
| WO | WO-0127160 A1 | 4/2001 |
| WO | WO-0158956 A2 | 8/2001 |
| WO | WO-03012061 A2 | 2/2003 |
| WO | WO-03100008 A2 | 12/2003 |
| WO | WO-2004023973 A2 | 3/2004 |
| WO | WO-2006013107 A1 | 2/2006 |
| WO | WO-2006124269 A2 | 11/2006 |
| WO | WO-2007072866 A1 | 6/2007 |
| WO | WO-2009100309 A2 | 8/2009 |
| WO | WO-2010065536 A2 | 6/2010 |
| WO | WO-2011028933 A1 | 3/2011 |
| WO | 2012162367 A1 | 11/2012 |
| WO | WO-2014036071 A1 | 3/2014 |
| WO | WO-2016145307 A1 | 9/2016 |
| WO | WO-2017156298 A1 | 9/2017 |
| WO | WO-2018034784 A1 | 2/2018 |
| WO | WO-2020023220 A1 | 1/2020 |
| WO | WO-2021011716 A1 | 1/2021 |
| WO | WO-2021011717 A1 | 1/2021 |
| WO | WO-2021113702 A1 | 6/2021 |
| WO | WO-2022098592 A1 | 5/2022 |
| WO | WO-2022098593 A1 | 5/2022 |
| WO | WO-2022192100 A1 | 9/2022 |
| WO | WO-2022192308 A1 | 9/2022 |
| WO | WO-2022203830 A1 | 9/2022 |
| WO | WO-2022212227 A1 | 10/2022 |
| WO | WO-2022235758 A1 | 11/2022 |
| WO | WO-2023016888 A1 | 2/2023 |
| WO | WO-2023016889 A1 | 2/2023 |
| WO | WO-2023016893 A1 | 2/2023 |
| WO | WO-2023016933 A1 | 2/2023 |
| WO | WO-2024026388 A1 | 2/2024 |
| WO | 2024126431 A1 | 6/2024 |

OTHER PUBLICATIONS

Accession P30273, 1993, pp. 1-2.

Ames, R. S., et al., "Conversion of murine Fabs isolated from a combinatorial phage display library to full length immunoglobulins," Journal of Immunological Methods, Aug. 18, 1995, 184(2), pp. 177-186.

Aruffo A., et al., "CD44 is the Principal Cell Surface Receptor for Hyaluronate," Cell, Jun. 29, 1990, vol. 61 (7), pp. 1303-1313.

Ashkenazi A., et al., "Protection Against Endotoxic Shock by a Tumor Necrosis Factor Receptor Immunoadhesin," Proceedings of the National Academy of Sciences of the United States of America, Dec. 1991, vol. 88, pp. 10535-10539.

Asselin-Paturel C., et al., "Mouse Strain Differences in Plasmacytoid Dendritic Cell Frequency and Function Revealed by a Novel Monoclonal Antibody," The Journal of Immunology USA, Dec. 2003, vol. 171, pp. 6466-6477, XP002984375.

Banham A.H., et al., "Identification of the CD85 Antigen as IL T2, an Inhibitory MHC Class I Receptor of the Immunoglobulin Superfamily," Journal of Leukocyte Biology, Jun. 1999, vol. 65, pp. 841-845.

Bianco P., et al., "Induction of Dendritic Cell Differentiation by IFN-alpha in Systemic Lupus Erythematosus," Science, Nov. 16, 2001, vol. 294, pp. 1540-1543.

Blasius A., et al., "A Cell-Surface Molecule Selectively Expressed on Murine Natural Interferon-Producing Cells that Blocks Secretion of Interferon-Alpha," Blood, Jun. 1, 2004, vol. 103, No. 11, pp. 4201-4206.

Brinkmann, U., et al., "Phage display of disulfide-stabilized Fv fragments," Journal of Immunological Methods, May 11, 1995, 182(1), pp. 41-50.

Burton D.R., et al., "Human Antibodies from Combinatorial Libraries," Advances in Immunology, Jan. 1994, vol. 57, pp. 191-280.

Butler J.E., "The Amplified ELISA: Principles of and Applications for the Comparative Quantitation of Class and Subclass Antibodies and the Distribution of Antibodies and Antigens in Biochemical Separates," Methods in Enzymology, 1981, vol. 73, Part B, pp. 482-523.

Byrn R.A., et al., "Biological Properties of a CD4 Immunoadhesin," Nature, Apr. 12, 1990, vol. 344, No. 6267, pp. 667-670.

Cao W., et al., "Signaling and Ligand Interaction of ILT7: Receptor-Mediated Regulatory Mechanisms for Plasmacytoid Dendritic Cells," Immunological Reviews, Mar. 2010, vol. 234, No. 1, pp. 163-176.

Cao W., et al., "Plasmacytoid Dendritic Cell-Specific Receptor ILT7-FcεRIγ Inhibits Toll-Like Receptor-Induced Interferon Production," Journal of Experimental Medicine, May 30, 2006, vol. 203, No. 6, pp. 1399-1405.

(56)         References Cited

OTHER PUBLICATIONS

Capon D.J., et al., "Designing CD4 Immunoadhesins for AIDS Therapy," Nature, Feb. 9, 1989, vol. 337, pp. 525-531.

Carrington M., et al., "The KIR Gene Cluster", National Center of Biotechnology Information, May 28, 2003, 171 pages.

Chapman A.P., "PEGylated Antibodies and Antibody Fragments for Improved Therapy: A Review," Advanced Drug Delivery Reviews, Jun. 17, 2002, vol. 54, No. 4, pp. 531-545.

Chen S., et al., "Ponatinib Protects Mice from Lethal Influenza Infection by Suppressing Cytokine Storm," Frontiers in Immunology, Jun. 2019, vol. 10 (1393), pp. 1-13.

Cho M., et al., "Sage Library Screening Reveals ILT7 as a Specific Plasmacytoid Dendritic Cell Marker That Regulates Type I IFNProduction," International Immunology, Jan. 2008, vol. 20, No. 1, pp. 155-164.

Chothia C., et al., "Canonical Structures for the Hypervariable Regions of Immunoglobulins," Journal of Molecular Biology, Aug. 20, 1987, vol. 196, No. 4, pp. 901-917.

Cockett M.I., et al., "High Level Expression of Tissue Inhibitor of Metalloproteinases in Chinese Hamster Ovary Cells Using Glutamine Synthetase Gene Amplification," Biotechnology, Jul. 1990, vol. 8, No. 7, pp. 662-667.

Colbere-Garapin F., et al., "A New Dominant Hybrid Selective Marker for Higher Eukaryotic Cells," Journal of Molecular Biology, Jul. 25, 1981, vol. 150 (1), pp. 1-14.

Colman P. M., "Effects of Amino Acid Sequence Changes on Antibody-Antigen Interactions," Biomolecular Research Institute, Jan. 1994, vol. 145, No. 1, pp. 33-36.

Colonna M., et al., "A Family of Inhibitory and Activating Ig-Like Receptors that Modulate Function of Lymphoid and Myeloid Cells," Seminars in Immunology, Apr. 2000, vol. 12, No. 2, pp. 121-127.

Crouse G.F., et al., "Expression and Amplification of Engineered Mouse Dihydrofolate Reductase Minigenes," Molecular and Cellular Biology, Feb. 1983, vol. 3, No. 2, pp. 257-266.

Dall'Acqua W.F., et al., "Antibody Humanization by Framework Shuffling," Methods, May 2005, vol. 36, No. 1, pp. 43-60.

Dashivets T., et al., "Oxidation in the Complementarity-Determining Regions Differentially Influences the Properties of Therapeutic Antibodies," MABs, November- Dec. 2016, vol. 8, No. 8, pp. 1525-1535.

Dayhoff M.O., et al., "A model of Evolutionary Change in Proteins", Chapter 22 in Atlas of Protein Sequence and Structure, National Biomedical Research Foundation, Washington DC, 1978, vol. 5 (3), pp. 345-352.

Dzionek A., et al., "BDCA-2, A Novel Plasmacytoid Dendritic Cell-specific Type II C-type Lectin, Mediates Antigen Capture and Is a Potent Inhibitor of Interferon Alpha/beta Induction," Journal of Experimental Medicine, 171 Dec. 2001, vol. 194, No. 12, pp. 1823-1834.

Edwards, B.M. et al., "The Remarkable Flexibility of the Human Antibody Repertoire; Isolation of Over One Thousand Different Antibodies to a Single Protein, BLyS," Journal of Molecular Biology, Nov. 14, 2003, 334(1, pp. 103-118.

Foecking M.K., et al., "Powerful and Versatile Enhancer-Promoter Unit for Mammalian Expression Vectors," Gene, Jan. 1986, vol. 45, No. 1, pp. 101-105.

Foote J., et al., "Antibody Framework Residues Affecting the Conformation of the Hypervariable Loops," Journal of Molecular Biology, Mar. 20, 1992, vol. 224 (2), pp. 487-499.

Gascoigne., et al., "Secretion of a Chimeric T-Cell Receptor-Immunoglobulin Protein," Proceedings of the National Academy of Sciences of the United States of America, May 1987, vol. 84, pp. 2936-2940.

Gentz R., et al., "Bioassay for Trans-Activation Using Purified Human Immunodeficiency Virus Tat-Encoded Protein: Trans-Activation Requires mRNA Synthesis," Proceedings of the National Academy of Sciences of the United States of America, Feb. 1989, vol. 86, pp. 821-824.

Hamers-Casterman C., et al., "Naturally Occurring Antibodies Devoid of Light Chains," Nature, Jun. 3, 1993, vol. 363, No. 6428, pp. 446-448.

Hoogenboom H.R., et al., "By-Passing Immunisation: Human Antibodies From Synthetic Repertoires of Germline VH Gene Segments Rearranged in Vitro," Journal of Molecular Biology, Sep. 20, 1992, vol. 227, No. 2, pp. 381-388.

Hopkins S.J., et al., "Cytokines in Synovial Fluid: II. The Presence of Tumour Necrosis Factor and Interferon," Clinical and Experimental Immunology, Jul. 1988, vol. 73, No. 1, pp. 88-92.

"Horizon Therapeutics pic Announces New Development Programs at Virtual R&D Day," Bloomberg, Sep. 29, 2021, 3 pages.

Horizon Therapeutics Pic, Virtual R&D Day Presentation, Sep. 29, 2021, 118 pages.

Horizon Therapeutics Pic, Virtual R&D Day Remarks, Sep. 29, 2021, 24 pages.

Inouye S., et al., "Up-Promoter Mutations in the Lpp Gene of *Escherichia coli*," Nucleic Acids Research, May 10, 1985, vol. 13, No. 9, pp. 3101-3110.

International Preliminary Report on Patentability for International Application No. PCT/US2021/025600, mailed Oct. 13, 2022, 12 pages.

International Search Report and Written Opinion for Application No. PCT/US2021/025600, mailed Oct. 5, 2021, 21 pages.

Jalkanen M., et al., "Cell Surface Proteoglycan of Mouse Mammary Epithelial Cells is Shed by Cleavage of its Matrix-Binding Ectodomain from its Membrane-Associated Domain," Journal of Cell Biology, Dec. 1987, vol. 105, pp. 3087-3096.

Jalkanen M., et al., "Heparan Sulfate Proteoglycans from Mouse Mammary Epithelial Cells: Localization on the Cell Surface with a Monoclonal Antibody," Journal of Cell Biology, Sep. 1985, vol. 101 (3), pp. 976-984.

Johnson et al., "Human Follicular Dendritic Cells a Study of Monoclonal Antibodies," Clinical and Experimental Immunology, Apr. 1986, vol. 64 (1), pp. 205-213.

Jones E.W., "Proteinase Mutants of *Saccharomyces cerevisiae*," Genetics, Jan. 1977, vol. 85, No. 1, pp. 23-33.

Jones P.T., et al., "Replacing the Complementarity-Determining Regions in a Human Antibody with those from a Mouse," Nature, May 1986, vol. 321, pp. 522-525.

Ju X-S., et al., "Immunoglobulin-like Transcripts ILT2, ILT3 and ILT7 Are Expressed by Human Dendritic Cells and Down-regulated Following Activation," Gene, Apr. 28, 2004, vol. 331, pp. 159-164.

Kameda Y., et al., "Production of a Monoclonal Antibody Against Cell-surface Glycoprotein of Guinea Pig Adrenocortical Cells," The Journal of Histochemistry and Cytochemistry, Feb. 1993, vol. 41, No. 2, pp. 235-243.

Kamogawa-Schifter Y., et al., "Ly49Q Defines 2 pDC Subsets in Mice," Blood, Apr. 1, 2005, vol. 105, No. 7, pp. 2787-2792.

Karnell et al., "Supplementary Materials for: Depleting plasmacytoid dendritic cells reduces local type I interferon responses and disease activity in patients with cutaneous lupus," May 26, 2021, Science Translational Medicine 13, eabf8442, DOI: 10.1126/scitranslmed. abf8442, 9 pages.

Karnell J.L., et al., "Depleting Plasmacytoid Dendritic Cells Reduces Local Type I Interferon Responses and Disease Activity in Patients With Cutaneous Lupus," Science translational Medicine, May 26, 2021, vol. 13, No. 595, 14 pages, DOI: 10.1126/scitranslmed. abf8442.

Kashihara M., et al., "A Monoclonal Antibody Specifically Reactive to Human Langerhans Cells," The Journal of Investigative Dermatology, Nov. 1986, vol. 87, pp. 602-607.

Ketileborough, C. A., et al., "Isolation of tumor cell-specific single-chain Fv from immunized mice using phage-antibody libraries and the re-construction of whole antibodies from these antibody fragments", European Journal of Immunology, Apr. 1994, 24(4), pp. 952-958.

Kingsman A.J., et al., "Replication in *Saccharomyces cerevisiae* of Plasmid pBR313 Carrying DNA from the Yeast Trpl Region," Gene, Oct. 1979, vol. 7, No. 2, pp. 141-152.

Klimka A., et al., "Human Anti-CD30 Recombinant Antibodies by Guided Phage Antibody Selection Using Cell Panning," The British Journal of Cancer, Jul. 2000, vol. 83, No. 2, pp. 252-260.

(56) References Cited

OTHER PUBLICATIONS

Kunkel T.A., et al., "Rapid and Efficient Site-Specific Mutagenesis Without Phenotypic Selection," Methods in Enzymology, 1987, vol. 154 pp. 367-382.

Kunkel T.A., "Rapid and Efficient Site-specific Mutagenesis Without Phenotypic Selection," Proceedings of the National Academy of Sciences USA, Jan. 1985, vol. 82(2), pp. 488-492.

Lefranc, M-P. et al., "IMGT unique numbering for immunoglobulin and T cell receptor variable domains and Ig superfamily V-like domains," Developmental & Comparative Immunology, Jan. 2003, 27(Issue 1), pp. 55-77.

Leong S.R., et al., "Adapting Pharmacokinetic Properties of a Humanized AntiInterleukin-8 Antibody for Therapeutic Applications using Site-Specific Pegylation," Cytokine, Nov. 2001, vol. 16, No. 3, pp. 106-119.

Lesslauer W., et al., "Recombinant Soluble Tumor Necrosis Factor Receptor Proteins Protect Mice from Lipopolysaccharide-Induced Lethality," European Journal of Immunology, Nov. 1991, vol. 21, No. 11, pp. 2883-2886.

Linsley P.S., et al., "Binding of the B Cell Activation Antigen B7 to CD28 Costimulates T Cell Proliferation and Interleukin 2 mRNA Accumulation," The Journal of Experimental Medicine, Mar. 1, 1991, vol. 173, No. 3, pp. 721-730.

Linsley P.S. et al., "CTLA-4 Is a Second Receptor for the B Cell Activation Antigen B7," The Journal of Experimental Medicine, Sep. 1991, vol. 174, pp. 561-569.

Lloyd, C., et al., "Modelling the human immune response: performance of a 1011 human antibody repertoire against a broad panel of therapeutically relevant antigens," Protein Engineering, Design and Selection, Mar. 2009, 22(3), pp. 159-168.

Lonberg N., et al., "Human Antibodies From Transgenic Mice," International Reviews of Immunology, Jan. 1995, vol. 13, pp. 65-93.

Lowy I., et al., "Isolation of Transforming DNA: Cloning the Hamster Aprt Gene," Cell, Dec. 1980, vol. 22 (3), pp. 817-823.

Mach H., et al., "Statistical Determination of the Average Values of the Extinction Coefficients of Tryptophan and Tyrosine in Native Proteins," Analytical Biochemistry, Jan. 1992, vol. 200, No. 1, pp. 74-80.

Maggio E.T., "Enzyme-Immunoassay," CRC Press Incorporated, Nov. 1980, 30 Pages.

Malleret B., et al., "Effect of SIVmac Infection on Plasmacytoid and CD1c+ Myeloid Dendritic Cells in Cynomolqus Macaques," Immunology, Jun. 2008, vol. 124, pp. 223-233, DOI:10.1111/j.1365-2567.2007.02758.x.

Marketos N., et al., "Type I Interferon Signature in Sjogren's Syndrome: Pathophysiological and Clinical Implications," Clinical and Experimental Rheumatology, Jul. 4, 2019, vol. 37 (3), No. 118, pp. 185-191.

Marks J.D., et al., "By-Passing Immunization: Human Antibodies from V-gene Libraries Displayed on Phage," Journal of Molecular Biology, Dec. 1991, vol. 222, pp. 581-597.

McCafferty J., et al., "Selection and Rapid Purification of Murine Antibody Fragments that Bind a Transition-State Analog by Phage Display," Biotechnology and Applied Biochemistry, May-Jun. 1994, vol. 47, No. 2-3, pp. 157-173.

Morgan R.A., et al., "Human Gene Therapy," Annual Review of Biochemistry, Jul. 1993, vol. 62, pp. 191-217.

Muller S., et al., "Spliceosomal Peptide P140 for Immunotherapy of Systemic Lupus Erythematosus: Results of an Early Phase II Clinical Trial," Arthritis & Rheumatism, Dec. 2008, vol. 58, No. 12, pp. 3873-3883, DOI:10.1002/art.24027.

Mulligan R.C., et al., "Selection for Animal Cells that Express the *Escherichia coli* Gene Coding for Xanthine-Guanine Phosphoribosyltransferase," Proceedings of the National Academy of Sciences of the United States of America, Apr. 1981, vol. 78, No. 4, pp. 2072-2076.

Mulligan R.C., "The Basic Science of Gene Therapy," Science, May 14, 1993, vol. 260, No. 5110, pp. 926-932.

Murphy et al., "Enhancing recombinant antibody performance by optimally engineering its format," Journal of Immunological Methods, Dec. 2018, (463), pp. 127-133.

Nakajima H., et al., "Cutting Edge: Human Myeloid Cells Express an Activating ILT Receptor (ILT1) That Associates with Fc Receptor gamma-Chain," Journal of Immunology, Jan. 1, 1999, vol. 162, No. 1, pp. 5-8.

Nelson P.N., et al., "Demystified Monoclonal Antibodies," Journal of Clinical Pathology, Jun. 2000, vol. 53, pp. 111-117.

Nestle F. O., et al., "Plasmacytoid Predendritic Cells Initiate Psoriasis Through Interferon-alpha Production," Journal of Experimental Medicine, Jul. 4, 2005, vol. 202, No. 1, pp. 135-143.

O'Hare K., et al., "Transformation of Mouse Fibroblasts to Methotrexate Resistance by a Recombinant Plasmid Expressing a Prokaryotic Dihydrofolate Reductase," Proceedings of the National Academy of Sciences of the United States of America, Mar. 1981, vol. 78 (3), pp. 1527-1531.

Ohtsuka M., et al., "NFAM1, an Immunoreceptor Tyrosine-Based Activation Motif-Bearing Molecule that Regulates B Cell Development and Signaling," Proceedings of the National Academy of Sciences of the United States of America, May 25, 2004, vol. 101, No. 21, pp. 8126-8131, DOI:10.1073/pnas.0401119101.

Orlando M., "Modification of Proteins and Low Molecular Weight Substances with Hydroxyethyl Starch (HES)," Inaugural Dissertation, Justus-Liebig-Universität Gießen, 2003, 191 pages.

Osbourn J.K., et al., "Generation of a Panel of Related Human ScFv Antibodies With High Affinities for Human CEA", Immunotechnology, Sep. 1996, 2(3), pp. 181-196.

Paul W.E., "Structure and Function of Immunoglobulins," Fundamental Immunology, 1993, 3rd Edition, Chapter 9, pp. 292-295.

Peppel K., et al., "A Tumor Necrosis Factor (TNF) Receptor-Igg Heavy Chain Chimeric Protein as a Bivalent Antagonist of TNF Activity," Journal of Experimental Medicine, Dec. 1, 1991, vol. 174 (6), pp. 1483-1489.

Perez A., et al., "Myasthenia Gravis Induced by Alpha-Interferon Therapy," American Journal of Hematology, Aug. 1995, vol. 49, No. 4, pp. 365-366.

Persic, L., et al., "An integrated vector system for the eukaryotic expression of antibodies or their fragments after selection from phage display libraries," Gene, Mar. 10, 1997, 187(1), pp. 9-18.

Presta L.G., "Antibody Engineering," Current Opinion in Structural Biology, Aug. 1992, vol. 2 (4), pp. 593-596.

Rattan S.I.S., et al., "Protein Synthesis, Posttranslational Modifications, and Aging," Annals of the New York Academy of Sciences, Nov. 1992, vol. 663, pp. 48-62.

Riechmann L., et al., "Reshaping Human Antibodies for Therapy," Nature, Mar. 1988, vol. 332, No. 24, pp. 323-327.

Rose N.R., "Prediction and Prevention of Autoimmune Disease in the 21st Century: A Review and Preview," American Journal of Epidemiology, vol. 183, No. 5, Mar. 1, 2016, pp. 403-406, DOI:10.1 093/aje/kwv292.

Rothe C., et al., "The Human Combinatorial Antibody Library HuCAL GOLD Combines Diversification of All Six CDRs According to the Natural Immune System with a Novel Display Method for Efficient Selection of High-Affinity Antibodies," Journal of Molecular Biology, Feb. 29, 2008, vol. 376, No. 4, pp. 1182-1200, DOI:0.1016/j.jmb.2007.12018.

Roux K.H., et al., "Comparisons of the Ability of Human IgG3 Hinge Mutants, IgM, IgE, and IgA2, to Form Small Immune Complexes: A Role for Flexibility and Geometry," The Journal of Immunology, Oct. 1998, vol. 161, pp. 4083-4090, Retrieved from URL: http://www.jimmunol.org/content/161/8/4083.

Rudikoff, S. et al., "Single amino acid substitution altering antigen-binding specificity," Proceedings of the National Academy of Sciences, USA, Mar. 1982, 79(6), pp. 1979-1983.

Ruther U., et al., "Easy Identification of cDNA Clones," The EMBO Journal, Jun. 27, 1983, vol. 2, No. 10, pp. 1791-1794.

Safdari Y., et al., "Antibody Humanization Methods—A Review and Update," Biotechnology and Genetic Engineering Reviews, Aug. 2013, vol. 29, No. 2, pp. 175-186.

Santerre R.F., et al., "Expression of Prokaryotic Genes for Hygromycin B and G418 Resistance as Dominant-Selection Markers in Mouse L Cells," Gene, Oct. 1984, vol. 30, No. 1-3, pp. 147-156.

(56) References Cited

OTHER PUBLICATIONS

Seifter S., et al., "Analysis for Protein Modifications and Nonprotein Cofactors," Methods in Enzymology, Jan. 1990, vol. 182, pp. 626-646.

Sheets M.D., et al., "Efficient Construction of a Large Nonimmune Phage Antibody Library: The Production of High-Affinity Human Single-Chain Antibodies to Protein Antigens," Proceedings of the National Academy of Sciences, USA, May 26, 1998, vol. 95 (11), pp. 6157-6162.

Shiozawa S., et al., "Interferon-alpha in Lupus Psychosis," Arthritis and Rheumatism, Apr. 1992, vol. 35, No. 4, pp. 417-422.

Smith T.F., et al., "Comparison of Biosequences," Advanced in Applied Mathematics, Dec. 1981, vol. 2, Issue 4, pp. 482-489.

Stamenkovic I., et al., "The B Lymphocyte Adhesion Molecule CD22 Interacts with Leukocyte Common Antigen CD45RO on T Cells and A2-6 Sialyltransferase, CD75, on B Cells," Cell, Sep. 20, 1991, vol. 66, pp. 1133-1144.

Stinchcomb D.T., et al., "Isolation and Characterisation of a Yeast Chromosomal Replicator," Nature, Nov. 1, 1979, vol. 282, pp. 39-43.

Szybalska E.H., et al., "Genetics of Human Cell Lines, IV. DNA-Mediated Heritable Transformation of a Biochemical Trait," Proceedings of the National Academy of Sciences, USA, Oct. 15, 1962, vol. 48, No. 12, pp. 2026-2034.

Szymkowski, David E., "Creating the next generation of protein therapeutics through rational drug design," Current Opinion Drug Discovery & Development, vol. 8, No. 5, Sep. 2005, pp. 590-600.

Thorpe P.E., et al., "The Preparation and Cytotoxic Properties of Antibody-Toxin Conjugates," Immunological Reviews, Feb. 1982, vol. 62, pp. 119-158.

Tolstoshev P., "Gene Therapy, Concepts, Current Trials and Future Directions," Annual Review of Pharmacology and Toxicology, Apr. 1993, vol. 33, pp. 573-596, Retrieved from URL: www.annualreviews. org.

Traunecker A., et al., "Highly Efficient Neutralization of HIV with Recombinant CD4-Immunoglobulin Molecules," Nature, May 4, 1989, vol. 339(6219), pp. 68-70.

Tschumper G., et al., "Sequence of a Yeast DNA Fragment Containing a Chromosomal Replicator and the TRP1 Gene," Gene, Jul. 1980, vol. 10, No. 2, pp. 157-166.

UNIPROT: "Leukocyte Immunoglobulin-Like Receptor Subfamily a Member 4," UniProtKB-P59901, Oct. 3, 2003, 11 Pages.

Vales-Gomez M., et al., "Genetic Variability of the Major Histocompatibility Complex Class I Homologue Encoded by Human Cytomegalovirus Leads to Differential Binding to the Inhibitory Receptor ILT2," Journal of Virology, Feb. 2005, vol. 79, No. 4, pp. 2251-2260.

Van Heeke G., et al., "Expression of Human Asparagine Synthetase in *Escherichia coli*," Journal of Biological Chemistry, Apr. 5, 1989, vol. 264, No. 10, pp. 5503-5509.

Vaughan T.J., et al., "Human Antibodies with Sub-nanomolar Affinities Isolated from a Large Non-immunized Phage Display Library," Nature Biotechnology, Mar. 1996, vol. 14, pp. 309-314.

Verhoeyen M., et al., "Reshaping Human Antibodies: Grafting an Antilysozyme Activity," Science, Mar. 25, 1988, vol. 239, No. 4847, pp. 1534-1536.

Viela B., "A Phase 1 Study of MEDI7734 in Type I Interferon-Mediated Autoimmune Diseases," Clinical Trails, NCT02780674, May 23, 2016, Retrieved from URL: https://clinicaltrials.gov/ct2/show/NCT02780674.

Wada M., et al., "Antithyroid Peroxidase Antibody and Development of Silent Thyroiditis during Interferon-alpha2a Treatment of Chronic Hepatitis C," The American Journal of Gastroenterology, Aug. 1995, vol. 90, No. 8, pp. 1366-1367.

Wang, Chunyan et al., "Preparation and Preliminary Identification of Anti-human ILT-4 Monoclonal Antibody," Chinese Journal of Cellular and Molecular Immunology, 2008, vol. 24, No. 3, pp. 238-239 (English Abstract provided).

Watson S.R., et al., "A Homing Receptor-IgG Chimera as a Probe for Adhesive Ligands of Lymph Node High Endothelial Venules," Journal of Cell Biology, Jun. 1990, vol. 110, No. 6, pp. 2221-2229.

Watson S.R., et al., "Neutrophil Influx into an Inflammatory Site Inhibited by a Soluble Homing Receptor-IgG Chimaera," Nature, Jan. 1991, vol. 349, pp. 164-167.

Weir A.N.C., et al., "Formatting Antibody Fragments to Mediate Specific Therapeutic Functions," Biochemical Society Transactions, Aug. 1, 2002, vol. 30, Part. 4, pp. 512-516.

Werth et al., "Targeting Plasmacytoid Dendritic Cells Improves Cutaneous Lupus Erythematosus Skin Lesions and Reduces Type I Interferon Levels: Results of a Phase 1 Study of VIB7734," [abstract]. Arthritis Rheumatology, 2020; 72 (suppl 10). https://acrabstracts. org/abstract/targeting-plasmacytoid-dendritic-cells-improves-cutaneous-lupu¬-erythematosus-skin-lesions-and-reduces-type-i-interferon-levels-results-of-a-phase-1-study-of-vib7734/, 2 pages.

Werth et al., "Targeting Plasmacytoid Dendritic Cells Improves Cutaneous Lupus Erythematosus Skin Lesions and Reduces Type I Interferon Levels: Results of a Phase 1 Study of VIB7734," [presentation]. Arthritis Rheumatology, 2020; 72 (suppl 10). https://acrabstracts.org/abstract/targeting-plasmacytoid-dendritic-cells-improves-cutaneous-lupus--erythematosus-skin-lesions-and-reduces-type-i-interferon-levels-results-of-a-phase-1-study-of-vib7734/. 17 pages.

Wigler M., et al., "Transfer of Purified Herpes Virus Thymidine Kinase Gene to Cultured Mouse Cells," Cell, May 1977, vol. 11, pp. 223-232.

Wilson I.A., et al., "The Structure of an Antigenic Determinant in a Protein," Cell, Jul. 1984, vol. 37, pp. 767-778.

Wilson L.E., et al., "Autoimmune Disease Complicating Antiviral Therapy for Hepatitis C Virus Infection," Seminars in Arthritis and Rheumatism, Dec. 2002, vol. 32, No. 3, pp. 163-173.

Wu et al., "An Analysis of the Sequences of the Variable Regions of Bence Jones Proteins and Myeloma Light Chains and Their Implications for Antibody Complementarity," Journal of Experimental Medicine, Mar. 1970, vol. 132 (2), pp. 211-250.

Wu G.Y., et al., "Delivery Systems for Gene Therapy," Biotherapy, Jan. 1991, vol. 3, pp. 87-95.

Young N.T., et al., "Conserved Organization of the ILT/LIR Gene Family Within the Polymorphic Human Leukocyte Receptor Complex," Immunogenetics, May-Jun. 2001, vol. 53, No. 4, pp. 270-278.

Zettlmeissl G., et al., "Expression and Characterization of Human CD4: Immunoglobulin Fusion Proteins," DNA and Cell Biology, Jun. 1990, vol. 9, No. 5, pp. 347-353.

Zurfluh L.L., "Auxin-Induced Changes in the Patterns of Protein Synthesis in Soybean Hypocotyl," Proceedings of the National Academy of Sciences of the United States of America, Jan. 1980, vol. 77, No. 1, pp. 357-361.

Amodio G. et al., "Dendritic cells: a double-edge sword in autoimmune responses. Front Immunol, vol. 3, No. 233, pp. 1-9 (2012).

Belousov U. V., Gurevich K. G. "Clinic pharmacokinetics," Drug dosing practice: Special edition of Series Rational pharmacotherapy, M.: Literra, 288 sh., (2005).

Davison et al., "New Treatments for Systemic Lupus Erythematosus on the Horizon: Targeting Plasmacytoid Dendritic Cells to Inhibit Cytokine Production", J Clin Cell Immunol, 8(6), doi:10.4172/2155-9899.1000534, (2017).

Ito, Plasmacytoid Dendritic cells and type I interferon as therapeutic cellular and molecular targets of autoimmune diseases, Cytometry Research 22 (1), pp. 37-46 (2012).

Mould D. R. et al. "Pharmacokinetics and pharmacodynamics of monoclonal antibodies," BioDrugs, vol. 24, No. 1, p. 23-39 (2010).

Skarlis C. et al. "Biologics in Sjogren's syndrome," Pharmacological Research. vol. 147, Art. No. 104389, (2019).

Tyagi R., Gupta I. N. "Use of c chemical modification and chemical cross-linking for stabilizing proteins (enzymes)," Biochemistry, vol. 63, N. 3., Edition 3, pp. 395-407 (1998).

Accession No. AF041261, 1999, pp. 1-2.

Olsen et al., "Alopecia areata investigational assessment guidelines—Part II. National Alopecia Areata Foundation", J Am Acad Dermatol. Sep. 2004; 51(3): 440-447.

(56) References Cited

OTHER PUBLICATIONS

Olsen et al., "Salt II: A new take on the Severity of Alopecia Tool (SALT) for determining percentage scalp hair loss". J Am Acad Dermatol. Dec. 2016; 75(6): 1268-1270.

Olsen et al., "Objective outcome measures: Collecting meaningful data on alopecia areata". J Am Acad Dermatol. Sep. 2018; 79(3): 470-478.e3.

Stroop S.D., et al., "Photosensitizers form in Histidine Buffer and Mediate the Photodegradation of a Monoclonal Antibody," Journal of Pharmaceutical Sciences, vol. 100, No. 12, Dec. 2011, pp. 5142-5155.

Cao et al., "Regulation of TLR 7/9 responses in plasmacytoid dendritic cells by BST2 and ILT7 receptor interaction", J Exp. Med. 206(7), pp. 1603-1614 (2009).

Greiff et al., "Quantitative assessment of the robustness of next-generation sequencing of antibody variable gene repertoires from immunized mice", BMC Immunology, vol. 15, pp. 1-14 (2014).

Janeway et al., "The generation of diversity in immunoglobulins", Immunobiology, 5th edition, New York: Garland Science (2001).

Lamot et al., "Methods for Type I interferon detection and their relevance for clinical utility and improved understanding of rheumatic diseases", Clinical and Experimental Rheumatology, vol. 37(6), pp. 1077-1083 (2019).

Palma et al., "Plasmacytoids dendritic cells are a therapeutic target in anticancer immunity", Biochimica et Biophysica Acta, 1826(2), pp. 407-414 (2012).

Rabia et al., "Understanding and overcoming trade-offs between antibody affinity, specificity, stability and solubility", Biochemical Engineering Journal, vol. 137, pp. 365-374 (2018).

* cited by examiner

IP= INVESTIGATIONAL PRODUCT (MEDI7734 OR PLACEBO); pDC = PLASMACYTOID DENDRITIC CELLS
SITES HAD THE OPTION OF BRINGING THE SUBJECT INTO THE INPATIENT UNIT TO STAY OVERNIGHT ON THE DAY BEFORE
RANDOMIZATION (DAY -1)

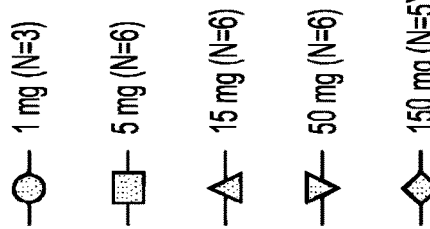
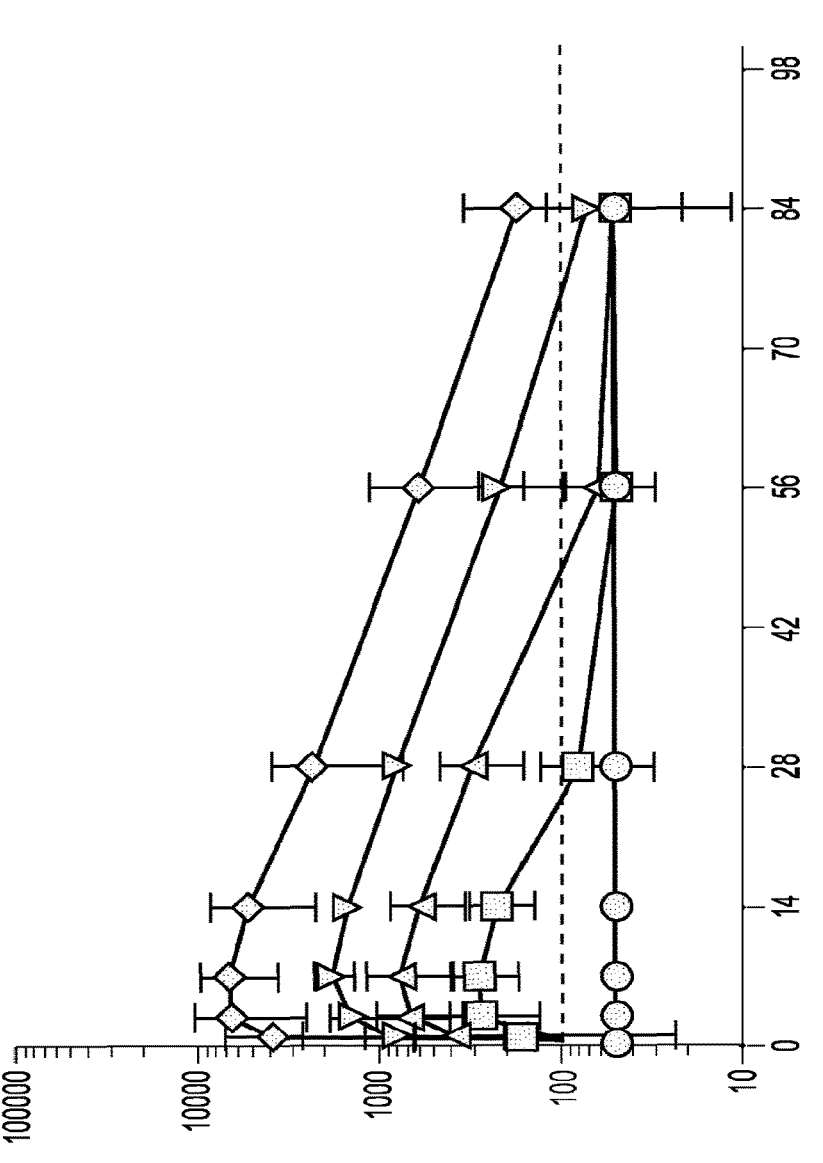
- DUE TO THE HIGH LLOQ, CONCENTRATIONS FROM 1 mg DOSE COHORT WERE ALL BLQ
- PK EXPOSURE INCREASED IN AN APPROXIMATELY DOSE-PROPORTIONAL MANNER OVER THE DOSE RANGE OF 1 TO 150 mg MEDI7734 SINGLE SC DOSE
- HALF-LIFE: RANGED FROM 13-20 DAYS AT 15-150 mg DOSE LEVELS
- NO ADA POSITIVE SAMPLES WERE DETECTED
*FIG. 3*

PERCENT OF BASELINE IN PDC LEVEL (%) OVER TIME
AS-TREATED POPULATION

ABSOLUTE PDC (CELLS/MICROL) OVER TIME
AS-TREATED POPULATION

ABSOLUTE pDC (CELLS/MICROL) (±SEM)

TIME (DAY)

PLACEBO
MEDI7734 15mg
MEDI7734 1mg
MEDI7734 50mg
MEDI7734 5mg
MEDI7734 150mg

ROLE OF PDCS IN THE PROGRESSION OF COVID-19 LUNG INJURY

FIG. 7

COMPARISON OF PDC DEPLETION VS BLOCKING IFNα OR IFNAR

|  | PDC DEPLETION | IFN-α BLOCKADE | IFNAR BLOCKADE |
|---|---|---|---|
| BLOCKADE OF ENDOGENOUS TYPE-1 IFN | • PARTIAL BLOCKADE OF ALL TYPE-1 IFNS (ONLY FROM PDC) | • NON-α TYPE-1 INTERFERONS NOT BLOCKED | • MOST COMPLETE BLOCKADE OF TYPE-1 IFN |
| IMPACT ON RISK OF OTHER VIRAL INFECTION | • LIMITED<br>• ANTIVIRAL EFFECT OF LOCALLY PRODUCED TYPE-1 IFN PRESERVED | • INCREASED<br>• BLOCKING IFN-α FORM ALL SOURCES KNOW TO INCREASE RISK OF OTHER VIRAL INFECTIONS) | • INCREASED<br>• LOSS OF ALL ANTIVIRAL EFFECT OF TYPE-1 INTERFERONS |
| BLOCKING EXOGENOUS TYPE-1 IFNS/POTENTIAL OF RESCUE WITH IFN RX | • NONE/RESCUE POTENTIAL RESERVED | • BLOCKS IFN-α BUT NOT IFN-β/RESCUE WITH IFN-β ONLY | • BLOCKS ALL TYPE-1 IFNS<br>• NO RESCUE |
| DIRECT REDUCTION IN THE PRODUCTION OF OTHER INFLAMMATORY CYTOKINES | • YES | • NO | • NO |

*FIG. 9*

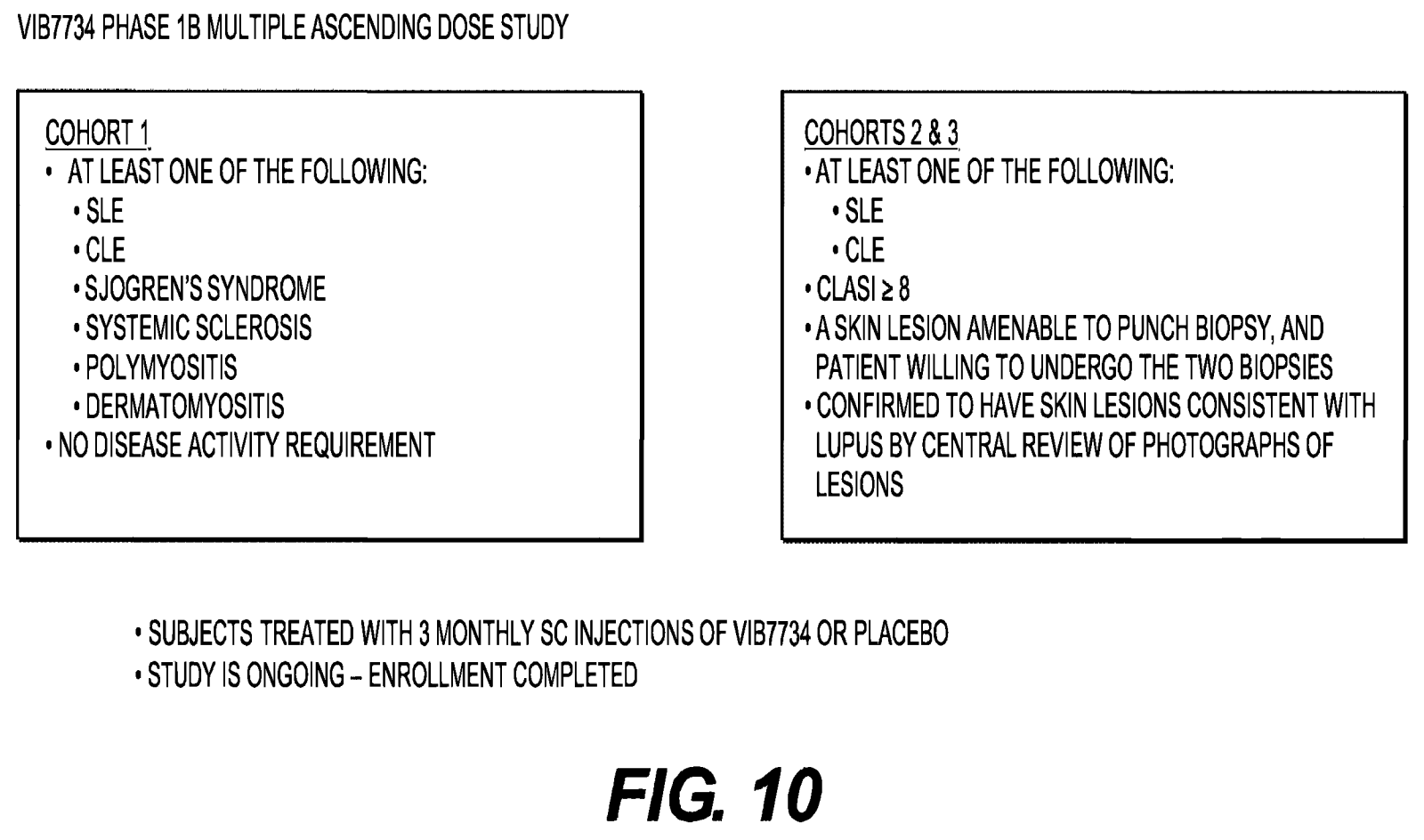

VIB7734 PHASE 1B MULTIPLE ASCENDING DOSE STUDY

COHORT 1
• AT LEAST ONE OF THE FOLLOWING:
  • SLE
  • CLE
  • SJOGREN'S SYNDROME
  • SYSTEMIC SCLEROSIS
  • POLYMYOSITIS
  • DERMATOMYOSITIS
  • NO DISEASE ACTIVITY REQUIREMENT

COHORTS 2 & 3
• AT LEAST ONE OF THE FOLLOWING:
  • SLE
  • CLE
• CLASI ≥ 8
• A SKIN LESION AMENABLE TO PUNCH BIOPSY, AND PATIENT WILLING TO UNDERGO THE TWO BIOPSIES
• CONFIRMED TO HAVE SKIN LESIONS CONSISTENT WITH LUPUS BY CENTRAL REVIEW OF PHOTOGRAPHS OF LESIONS

• SUBJECTS TREATED WITH 3 MONTHLY SC INJECTIONS OF VIB7734 OR PLACEBO
• STUDY IS ONGOING – ENROLLMENT COMPLETED

*FIG. 10*

SEQUENCE LISTING

```
Sequence total quantity: 2
SEQ ID NO: 1              moltype = AA  length = 122
FEATURE                  Location/Qualifiers
source                   1..122
                         mol_type = protein
                         organism = synthetic construct
SEQUENCE: 1
QVQLQQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARNG LWGWDSDAFD IWGRGTLVTV  120
SS                                                                122

SEQ ID NO: 2              moltype = AA  length = 110
FEATURE                  Location/Qualifiers
source                   1..110
                         mol_type = protein
                         organism = synthetic construct
SEQUENCE: 2
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTVV FGGGTKVTVL             110
```

METHODS OF TREATING IMMUNE-MEDIATED PULMONARY INJURY WITH AN ANTI-ILT7 ANTIBODY

CROSS REFERENCE TO RELATED APPLICATIONS

This application is a continuation of International Patent Application No. PCT/US2021/025600, filed Apr. 2, 2021 which is entitled to and claims benefit of priority to U.S. Provisional Patent Application No. 63/004,866 filed Apr. 3, 2020, U.S. Provisional Patent Application No. 63/052,596 filed Jul. 16, 2020 and U.S. Provisional Patent Application No. 63/066,955 filed Aug. 18, 2020, each of which is incorporated herein by reference in their entireties.

REFERENCE TO AN ELECTRONIC SEQUENCE LISTING

The contents of the electronic sequence listing (HOPA_028_03US_SeqList_ST26.xml; Size: 3,022 bytes; and Date of Creation: Sep. 30, 2022) is herein incorporated by reference in its entirety.

FIELD OF THE DISCLOSURE

The present disclosure relates to methods for treating or preventing immune-mediated pulmonary injury (IMPI) in a subject in need thereof, the method comprising administering to the subject an anti-Type I interferon (anti-T1i) therapy that blocks the activity, function or production of Type I interferon (T1i) in the subject, wherein the anti-T1i therapy is administered to the subject infected with a respiratory virus that causes a delayed T1i response in the subject.

BACKGROUND OF THE DISCLOSURE

The type I interferon (IFN) axis is one of the most significant pathways in human disease, and its dysregulation can be central to the pathogenesis of tissue injury associated with an exaggerated immune response. For example, acute lung injury (ALI) in Severe Acute Respiratory Syndrome-CoV (SARS-CoV), Middle Eastern Respiratory Syndrome (MERS) and Severe Acute Respiratory Syndrome Cov-2 (SARS-CoV-2 or "COVID-19") all have highly similar clinical courses that are caused by a systemic hyperinflammatory responses. It is well-known that Type-1 Interferons (IFNs) are central in driving the innate immune response in animal models of SARS-CoV, which mimic human SARS pneumonia. In these animal models, the presence of plasmacytoid dendritic cells (pDCs) in the respiratory tract is increased, and these pDCs produce high levels of Type 1 IFNs and other inflammatory mediators, such as but not limited to TNF-α and inflammatory macrophages. In addition, inflammatory macrophages (IMM) overexpressing Type-1 IFN induced genes are expanded in bronchoalveolar lavage fluid (BALF) in animal models of ALI from SARS-CoV infection. Thus blocking Type-1 IFNs and and/or depleting pDCs and/or IMM may provide a therapeutic benefit to subjects suffering from or at risk of suffering from IMPI due to a delayed Type 1 interferon reaction that is often accompanied by a respiratory virus infection.

SUMMARY OF THE DISCLOSURE

The present disclosure relates to methods for treating or preventing immune-mediated pulmonary injury (IMPI) in a subject in need thereof, the method comprising administering to the subject an anti-Type I interferon (anti-T1i) therapy that blocks the activity, function or production of Type I interferon (T1i) in the subject, wherein the anti-T1i therapy is administered to the subject infected with a respiratory virus that causes a delayed T1i response in the subject.

The present disclosure relates to methods for treating or preventing immune-mediated pulmonary injury (IMPI) in a subject in need thereof, the method comprising administering to the subject an antibody or antibody fragment that binds to immunoglobulin-like transcript 7 (ILT7) protein.

BRIEF DESCRIPTION OF THE FIGURES

FIG. 3 shows the mean serum concentration profile of the Anti-ILT7 therapy of the disclosure following a single subcutaneous dose in a subject suffering from at least one of the following five autoimmune diseases: SLE, Sjögren's syndrome, dermatomyositis, polymyositis, or systemic sclerosis.

Figure 7:
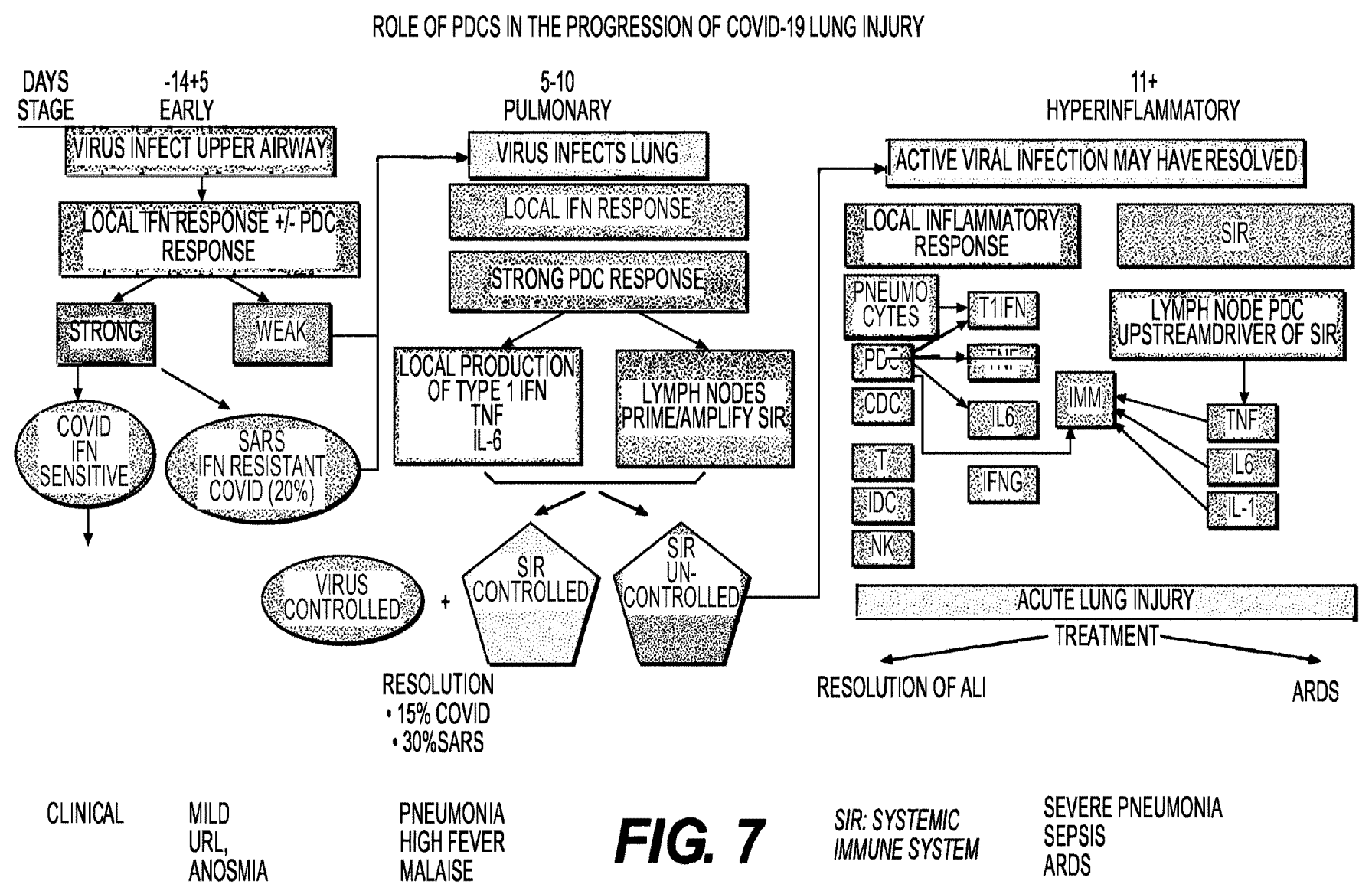

FIG. 7 shows the role of pDCs in the progression of IPMI caused by SARS-CoV-2.

FIG. 9 shows a comparison of different therapeutic strategies for treating or preventing IMPI in subjects infected or suspected of being infected or at risk of being infected with a respiratory virus that causes a delayed T1i reaction.

FIG. 10 shows different cohorts of a VIB7734 single ascending dose study

DETAILED DESCRIPTION OF THE DISCLOSURE

Figure 1:
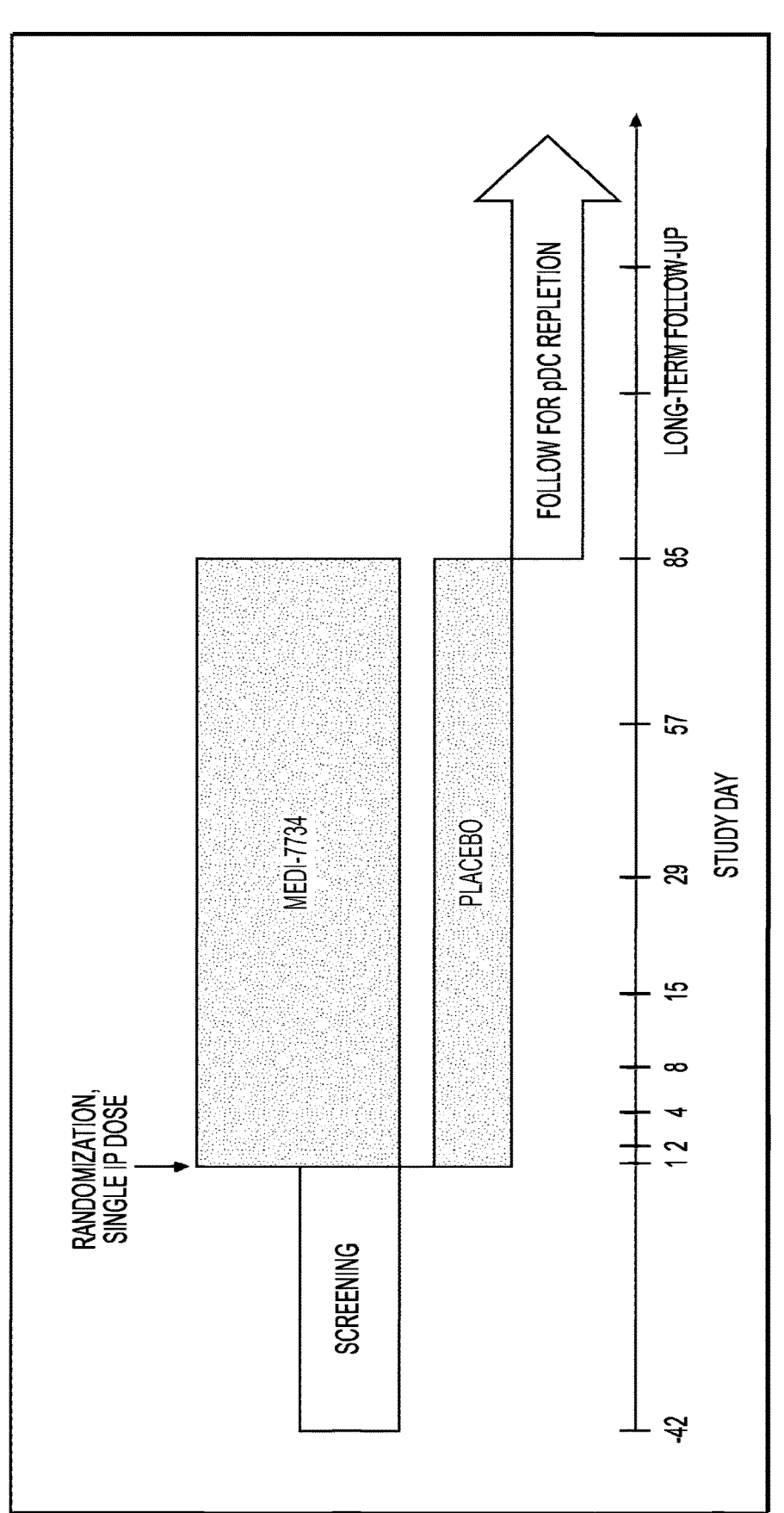
FIG. 1 shows the overall study design for a Phase I, randomized, blinded, placebo-controlled study to evaluate the safety and tolerability of single-ascending subcutaneous doses of the Anti-ILT7 therapy of the disclosure in subjects suffering from at least one of the following five autoimmune diseases: systemic lupus erythematosus (SLE), Sjögren's syndrome, dermatomyositis, polymyositis, or systemic sclerosis.

The present disclosure relates to methods for treating or preventing immune-mediated pulmonary injury (IMPI) in a subject in need thereof, the method comprising administering to the subject an anti-Type I interferon (anti-T1i) therapy that blocks the activity, function or production of Type I interferon (T1i) in the subject, wherein the anti-T1i therapy is administered to the subject infected with a respiratory virus that causes a delayed T1i response in the subject.

The present disclosure additionally relates to methods for treating a subject infected with Severe Acute Respiratory Syndrome-coronavirus-2 (SARS-CoV-2), the method comprising administering to the subject an antibody or antibody fragment that binds to immunoglobulin-like transcript 7 (ILT7) protein.

As used herein, the term immune-mediated pulmonary injury (IMPI) means an acute inflammatory condition causing damage or disruption to lung endothelium and lung epithelium. In one embodiment, the IMPI is acute lung injury (ALI). In another embodiment, the IMPI is acute respiratory distress syndrome (ARDS). The American-European Consensus Conference Committee (AECCC) defines ALI as an "acute lung disease with bilateral pulmonary infiltrate in a chest radiograph consistent with the presence of edema and no clinical evidence of left atrial hypertension; or (if measured) a pulmonary wedge pressure of 18 mmHg or less. Additionally, the ratio of arterial oxygen to the fraction of inspired oxygen ($PaO_2/FiO_2$) must be 300 mmHg or less, regardless of the level of positive end-expiratory pressure (PEEP)." Ragaller, M. and Richter, T., *J. Emerg. Trauma Shock*, 3(1):43-51 (2010) (incorporated by reference in its entirety). The AECCC also defines ARDS as a more severe form of ALI a $PaO_2/FiO_2$ of 200 mmHg or less. See, Ragaller, M. and Richter, T., *J. Emerg Trauma Shock*, 3(1):43-51 (2010). See also Johnson, E. and Matthay, M., *J. Aerosol. Med. Pulm. Drug Deliv.* 23(4): 243-252 (2010) (incorporated by reference in its entirety). In some embodiments, the subject with IMPI is infected with SARS-CoV-2. In further embodiments, the subject is infected with SARS-CoV-2 and has an ALI.

In other embodiments, the IMPI that is to be treated or prevented need not present every clinical marker of ALI or ARDS. In other embodiments, it is not necessary that ALI nor ARDS be affirmatively diagnosed or confirmed prior to beginning the therapeutic regimens described herein, provided that the attending physician detects or suspects an inflammatory condition that will or may disrupt the subject's lung endothelium and lung epithelium.

For example, according to the methods of the present disclosure, the anti-T1i therapies described herein can be administered to the subject after the subject has developed at least one clinical sign of an exaggerated immune response. As used herein, an "exaggerated immune response" means an imbalance in a subject's immune response to a foreign antigen. As one of skill in the art will appreciate, the immune system normally exists in a state of homeostasis such that the subject's immune response to a foreign antigen is limited in time and duration to prevent or avoid damage to the subject. An exaggerated immune response, therefore, is used to mean that the subject's immune in response to a foreign antigen is more extensive or longer or both, compared to a normal immune response. A more extensive immune response can mean, for example, that the subject's immune system produces higher than normal levels of pro-inflammatory cytokines or that subject's immune system produces lower than normal levels of anti-inflammatory cytokines. Accordingly, in specific embodiments, at least one clinical sign of an exaggerated immune response is higher than normal levels of pro-inflammatory cytokines or lower than normal levels of anti-inflammatory cytokines. In another example, a more extensive immune response can also mean that the subject's immune system induces or causes a higher accumulation of immune cells, e.g., innate immune cells, at the site of infection than normal. Accordingly, in specific embodiments, at least one clinical sign of an exaggerated immune response is a higher than normal accumulation of immune cells, e.g., innate immune cells, at the site of infection than normal. One of skill in the art will understand the difference between an innate and adaptive immune response. In one specific embodiment, the at least one clinical sign of an exaggerated immune response is not a clinical sign of exaggerated adaptive immune response, i.e., is not a sign or symptom an autoimmune disease.

As noted above, according to the methods of the present disclosure, the anti-T1i therapies described herein can be administered to the subject after the subject has developed at least one clinical sign of an exaggerated immune response. Signs of an exaggerated innate immune response include but are not limited to increased circulating levels of at least one pro-inflammatory cytokine, increased local levels of at least one pro-inflammatory cytokines, T-cell lymphopenia and an increase of at least one inflammatory marker. Examples of pro-inflammatory cytokines include but are not limited to interleukin (IL)-1, IL-2, IL-6, IL-8, IL-12, IL-18, tumor necrosis factor (TNF) and interferon-γ (IFNg). One of skill in the art will be familiar with identity of pro-inflammatory cytokines. One of skill in the art will also be familiar with typical inflammatory markers, such as but not limited to, circulating or local levels of C-reactive protein (CRP), circulating or local levels of lactate dehydrogenase (LDH), circulating or local levels of D-dimer, circulating or local levels of ferritin, circulating or local levels of procalcitonin (PCT) and erythrocyte sedimentation rate (ESR). Other markers of inflammation include but are not limited to circulating troponin levels and circulating levels of N-terminal pro B-type natriuretic peptide (NT-proBP).

In one embodiment, the anti-T1i therapy is administered to the subject after the subject exhibits at least one clinical marker of IMPI. As used herein, the term "clinical marker" is used to mean a clinical symptom or a clinical sign of a disease or abnormal condition. As clinical symptom is a physical parameter, such as breathing rate, heartbeat, blood pressure, $PaO_2/FiO_2$, that often causes subject discomfort or pain or an abnormal feeling. As used herein a clinical sign is a physiological parameter that may or may not be quantifiable or measurable in an absolute manner and may or may not cause subject discomfort or pain or an abnormal feeling. Examples of clinical signs of IMPI include but are not limited to abnormal chest imaging and transaminitis. Other examples of clinical signs of IMPI include but are not limited to clinical signs of an exaggerated immune response.

As used herein, the term "treat," or "treating" refers to an amelioration of a disease, disorder or abnormal condition, e.g., IMPI, or at least one discernible clinical marker thereof.

In one specific embodiment, "treatment" or "treating" refers to an alteration of at least one measurable clinical marker not necessarily discernible to the subject. In another embodiment, "treatment" or "treating" refers to inhibiting the progression of a disease, disorder or abnormal condition, e.g., IMPI, either physically, e.g., stabilization of a clinical symptom, physiologically, e.g., stabilization of clinical sign, or both. In yet another embodiment, "treatment" or "treating" refers to delaying the onset of a disease, disorder or abnormal condition, e.g., IMPI, or marker thereof.

As used herein, the term "prevent," "prevention," or "preventing" refers to reducing the risk or reducing the likelihood of acquiring a given disease, disorder or abnormal condition. The term prevent as used herein is not necessarily as a guarantee that the anti-T1i therapy will ensure that a subject at risk of developing IMPI will not develop or acquire IMPI. Instead, in one embodiment, the term prevent indicates the timing of the administration of the anti-T1i therapy to the subject such that the subject has not been diagnosed with having IMPI. In another embodiment, the term prevent indicates the timing of the administration of the anti-T1i therapy to the subject such that the subject is not exhibiting any clinical sign or clinical symptom of IMPI. In another embodiment, the therapies described in the present disclosure are administered as a preventative measure to a high-risk subject that is at risk of developing immune-mediated pulmonary injury (IMPI). In additional embodiments, the therapies described herein are administered to a subject to treat or prevent symptoms of SARS-CoV-2 infection. In certain additional embodiments, the therapies described herein are administered to a subject infected with SARS-CoV-2. In further embodiments, the therapies described herein are administered to a subject is infected with SARS-CoV-2 and exhibits signs or symptoms of ALI.

Accordingly, in specific embodiments of the methods of the present disclosure, an anti-T1i therapy is administered to the subject before the subject has developed at least one symptom of an exaggerated immune response or at least one clinical marker of IMPI. For example, when the anti-T1i therapies described herein are administered to the subject before the subject has developed at least one symptom of an exaggerated immune response or at least one clinical marker of IMPI, the subject may be a high-risk subject. As used herein, the terms subject and patient are interchangeably and means a human or non-human mammal, such as but not limited to household pets or farming animals such as but not limited to cats, dogs, swine, cattle, sheep, goats, horses, rabbits. Subjects also include non-human primates, such as but not limited to monkeys, chimpanzee and apes. The subject or patient must have an immune system capable of generating an exaggerated innate immune response. As used herein, the term "normal subject" refers to a healthy individual not affected with any disease or abnormal condition. The term "normal subject" also refers to an individual prior to exhibiting any signs or symptoms of an exaggerated immune response or IMPI.

As used herein, the term high-risk subject is subject that has a higher risk than normal for being infected with a respiratory virus or has a higher risk than normal for developing an exaggerated immune response. In specific embodiments, the high risk-subject is a human subject that is at least 60 years of age or is a subject with a pre-existing respiratory condition. A pre-existing respiratory condition includes but is not limited to asthma, chronic obstructive pulmonary disease (COPD), bronchitis, chronic bronchitis, emphysema, lung cancer, cystic fibrosis/bronchiectasis or pneumonia.

High-risk subjects also include subjects that regularly smoke or inhale tobacco, other plant material or other compounds, smoke or inhale vapor-based products. High-risk subjects also include immunocompromised subjects. Immunocompromised subjects are subjects with a decreased ability to establish an immune response to a foreign antigen. The subject may be immunocompromised because of a pre-existing condition, such as but not limited to cancer, HIV infection, diabetes, other genetic disorders and mal-nourishment to name a few. The subject may also be immunocompromised due to receiving treatment for another condition, such as radiation treatment, immunosuppressant treatment, e.g., for transplant or autoimmune patients.

According to the methods of the present disclosure, the therapies are administered to a subject that has been infected, or is suspected of being infected, with a respiratory virus that causes, or is capable of causing, a delayed Type 1 interferon (T1i) response in the subject. The subject need not be experiencing a delayed T1i response for the therapies to be administered.

In specific embodiments, the respiratory virus that causes or is capable of causing a delayed T1i response in the subject is a rhinovirus, an adenovirus, an influenza virus, a respiratory syncytial virus, enterovirus D68 and a coronavirus (CoV). Examples of respiratory CoVs that cause or are capable of causing a delayed T1i response in the subject include but are not limited to Severe Acute Respiratory Syndrome-Coronoavirus (SARS-CoV), Middle Eastern Respiratory Syndrome-coronavirus (MERS-CoV) and Severe Acute Respiratory Syndrome-coronavirus-2 (SARS-CoV-2). In one specific embodiment, the therapies described in the present disclosure are administered to a subject that has been infected or is suspected of being infected or is at risk of being infected, with SARS-CoV-2. In one specific embodiment, the therapies described in the present disclosure are administered to a subject that has been infected or is suspected of being infected or is at risk of being infected, with SARS-CoV. In one specific embodiment, the therapies described in the present disclosure are administered to a subject that has been infected or is suspected of being infected or is at risk of being infected, with MERS-CoV.

As used herein, a T1i response means an innate immune reaction in response to a foreign antigen. Typically, innate immune cells encounter a foreign antigen and immediately, e.g., within 3 hours or even sooner, and begin producing Type 1 IFNs and initiate an Interferon-induced Gene Signature (IFNGS) in response to the antigen. Typically, a normal T1i response is coordinated in such a way that peak IFN levels and/or IFNGS signaling occurs before peak virus titer levels. A "delayed T1i" response, on the other hand, is an innate immune response that is a delayed or slower than normal T1i response such that peak virus titers in the subject occur before peak T1i levels and/or peak IFNGS. See Channappanavar, R., et al., *Cell Host & Microbe*, 19:181-193 (2016), which is incorporated by reference in its entirety. For example, in a delayed T1i response, the levels of Type 1 IFN and/or the IFNGS may not be detectable for up to 24 hours, or later, post infection.

As used herein, the term "administer" or "administering" means introducing at least one therapy to a subject. When administration is for the purpose of treatment, the therapy is provided at, or after the onset of, at least one clinical marker of IMPI. The administration of the treatment therapy serves to attenuate any symptom or sign, or to prevent additional symptoms or signs from arising. When administration is for the purposes of preventing IMPI ("prophylactic administration"), the therapy is provided in advance of any visible or detectable symptom or sign of IMPI. The prophylactic administration of the therapy serves to attenuate subsequently arising symptoms or signs of IMPI, or to prevent symptoms or signs of IMPI from arising altogether.

The route of administration of any of the anti-T1i therapies disclosed herein are well known in the art. Exemplary routes of administering of the anti-T1i therapies described herein include, but are not limited to, parenteral, oral, mucosal, topical, transdermal, inhalation, sublingual, buccal, rectal, vaginal, and intranasal. The term parenteral, as used herein, includes subcutaneous injections, intravenous, intramuscular, intrasternal injection or infusion techniques. In specific aspects, the anti-T1i therapies used in the methods of the present disclosure are administered to a subject by subcutaneous injection. The term "administer," "administration," or "administering" may involve a single administration of an the anti-T1i therapies described herein, or multiple administrations of the anti-T1i therapies described herein. Multiple administration involves at least two, e.g., 2, 3, 4, 5, 6, 7, 8, 9, 10, or more administrations to a subject of at least one of the anti-T1i therapies described herein.

The therapies that are administered to the subject according to the methods of the present disclosure are anti-Type 1 interferon therapies. As used herein, the term "anti-Type 1 interferon therapy" means a therapy that is designed to reduce the activity, function or levels of endogenous Type 1 interferons (IFNs) that are normally produced by the innate immune system in response to a foreign antigen. Type 1 interferons are well-known in the art and include but are not limited to IFN-$\alpha$ (IFNa), IFN-$\beta$ (IFNb), IFN-$\kappa$ (IFNk), IFN-$\delta$ (IFNd), IFN-$\epsilon$ (IFNe), IFN-$\tau$ (IFNt), IFN-$\omega$ (IFNo), IFNv (IFNv) and IFN-$\zeta$ (IFNz). Type 1 IFNs are produced by several cells, with plasmacytoid cells (pDCs) being the one of the more robust Type 1 IFN producers. Type 1 IFNs are known to stimulate other innate cells, such as macrophages and natural killer (NK) cells to generate an anti-viral response, often involving the interferon regulatory factor (IRF) 3, 5 and/or 7 pathway(s).

An anti-T1i therapy, therefore, is used to mean a therapeutic regimen designed to interfere with the activity, function or levels of Type 1 IFNs. In one embodiment, the therapy is a therapy that blocks the activity, function or levels of IFNa. In a more specific embodiment, the anti-T1i therapy is an antibody or antibody fragment that binds to IFNa, thereby decreasing the activity or function of IFNa. In an even more specific embodiment, the antibody or fragment thereof that binds to IFNa is sifalimumab or a fragment thereof. Sifalimumab is an antibody that binds to a portion of IFNa, thus preventing the IFNa from binding to its receptor and thereby decreasing the activity or function of IFNa.

Other anti-IFNa antibodies or fragments thereof that can be used in connection with the methods of the present disclosure include but are not limited to antibodies described in U.S. Pat. No. 7,741,449, 9F3 and other antibodies described in U.S. Pat. No. 7,087,726, such as but not limited to Examples 1 and 2 and those disclosed in Tables 3 and 4, as well as those disclosed in the table entitled "Deposit of Material" on lines 25-54, column 56 of the 726 patent, all of which are incorporated by reference in their entirety. Still more antibodies specific for IFNa include but are not limited to NK-2 and YOK5/19 as disclosed in PCT Publication No. WO 84/03105, LO-22, disclosed in U.S. Pat. No. 4,902,618, 144 BS, disclosed in U.S. Pat. No. 4,885,166, and EBI-1, EBI-2, and EBI-3, disclosed in European Patent No. 119476, all of which are incorporated by reference in their entirety.

In another embodiment, the anti-T1i therapy is an antibody or antibody fragment that binds to interferon $\alpha/\beta$ receptor (IFNAR), thus preventing the IFN from binding to its receptor and thereby reducing the activity, function or production of the IFN in the subject. All Type 1 IFNs are known to bind to INFAR, thus administering a therapy that blocks INFAR would block the activity of most or all species of Type 1 IFNs. In one specific embodiment, the anti-IFNAR antibody or antibody fragment that is administered to the subject is anifrolumab or a fragment thereof, which is disclosed in U.S. Pat. No. 7,662,381. Pharmaceutical formulations of anifrolumab are disclosed in PCT Publication No. WO 2017/031288, which is hereby incorporated by reference in its entirety.

Other anti-IFNAR antibodies or fragments thereof that can be used in connection with the methods of the present disclosure include but are not limited to antibodies disclosed in U.S. Pat. Nos. 7,662,381, 7,619,070, 7,888,484 and 8,758,757, as well as PCT International Application No. PCT/US2009/033358, all of which are incorporated by reference in its entirety.

In certain embodiments, the anti-T1i therapy is antibody or antibody fragment that binds to blood dendritic cell-specific antigen 2 (BDCA-2), thus inhibiting the induction of IFN $\alpha/\beta$ expression in pDCs. In specific embodiments, the anti-BDCA-2 antibody is a monoclonal antibody. In more particular embodiments, the anti-BDCA-2 antibody is BIIB059/24F4A. See *EMBO Mol Med* 2015 April; 7(4):464-76, which is incorporated by reference in its entirety.

In another specific embodiment, the therapy is an antibody or antibody fragment that binds to immunoglobulin-like transcript 7 (ILT7) protein present on plasmacytoid dendritic cells (pDCs). Binding to the ILT7 protein can inhibit the function or activity of pDCs. In some embodiments, the anti-ILT7 therapies administered according to the methods of the present disclosure bind to full-length ILT7. In other embodiments, the anti-ILT7 therapies administered according to the methods of the present disclosure bind to a fragment of ILT7. In additional embodiments, the anti-ILT7 therapies administered according to the methods of the present disclosure binds to the extracellular domain of ILT7, located on pDCs. As noted earlier, pDCs are a major contributor to Type 1 interferon production, thus inhibiting the activity or function of pDCs will reduce the circulating and/or local levels of Type 1 interferons. In one specific embodiment, the anti-ILT7 antibody or antibody fragment is VIB7734 antibody or a fragment thereof. VIB7734 is described in PCT Application No. PCT/US2017/021616, which is incorporated by reference in its entirety. Specifically, VIB7734 is identified as clone ILT70137 in PCT Application No. PCT/US2017/021616. In another embodiment, VIB7734 is also an antibody comprising a heavy chain variable region (VH) of SEQ ID NO:1 and a light chain variable region (VL) of SEQ ID NO:2 herein.

```
                                      (SEQ ID NO: 1)
QVQLQQSGAEVKKPGASVKVSCKASGYTFTSYGISWVRQAPGQGLEWMG
WISAYNGNTNYAQKLQGRVTMTTDTSTSTAYMELRSLRSDDTAVYYCAR
NGLWGWDSDAFDIWGRGTLVTVSS (SEQ ID NO: 2)
QSALTQPASVSGSPGQSITISCTGTSSDVGGYNYVSWYQQHPGKAPKLM
IYDVSNRPSGVSNRFSGSKSGNTASLTISGLQAEDEADYYCSSYTSSST
VVFGGGTKVTVL
```

In some embodiments, the methods disclosed herein comprise administering VIB7734 to a subject with infected with SARS-CoV-2. In certain embodiments, the methods herein comprise administering an antibody comprising a heavy chain variable region (VH) of SEQ ID NO:1 and a light chain variable region (VL) of SEQ ID NO:2 as disclosed herein to a subject infected with SARS-CoV-2. In certain embodiments, the methods herein comprise administering an antibody comprising a heavy chain variable region (VH) at least about 95%, 96%, 97%, 98%, or 99% identical to SEQ ID NO:1 and a light chain variable region (VL) at least about 95%, 96%, 97%, 98%, or 99% identical to SEQ ID NO:2 disclosed herein to a subject infected with SARS-CoV-2.

Administration of VIB7734 or a fragment thereof to the subject in need of treatment will deplete levels of circulating or respiratory pDCs, thereby reducing the levels of circulating or local Type 1 IFNs in the subject. In particular, and without having to be bound by theory, VIB7734 and other anti-ILT7 antibodies described in PCT/US2017/021616 bind to ILT7 that is present on pDCs and to prevent binding of CD16. CD16 is a cell surface protein present in natural killer (NK) cells. The binding of the anti-ILT7 antibodies on the pDCs induces a depletion of local and/or circulating pDCs by inducing antibody-dependent cell-mediated cytotoxicity (ADCC) of the pDCs. In one specific embodiment, this anti-ILT7 induced reduction of circulating or local, e.g., respiratory, pDCs is reversible. The anti-ILT7 antibodies or fragments thereof used in the methods of the present disclosure, e.g., VIB7734, may comprise fucose moieties in the Fc region, or the antibodies or fragments thereof may be afucosylted.

In some embodiments, the reduction in pDCs in the subject is about 1% to about 100% compared to the pDCs in the subject prior to administration of the anti-ILT7 therapy described herein. In certain aspects, the a reduction in pDCs in the subject is at least about 1%, at least about 2%, at least about 5%, at least about 10%, at least about 20%, at least about 30%, at least about 30%, at least about 40%, at least about 50%, at least about 60%, at least about 70%, at least about 80%, at least about 90%, at least about 95%, at least about 96%, at least about 97%, at least about 98%, at least about 99%, or about 100% compared to pDCs in the subject prior to administration of the anti-ILT7 therapy described herein. In specific embodiments, the reduction in pDCs in the subject is at least about 50% compared to pDCs in the subject prior to administration of the anti-ILT7 therapy described herein. In certain aspects, the pDCs are circulating pDCs.

In certain embodiments, administration of a therapeutically effective amount of the anti-ILT7 therapy described herein to a subject in need thereof causes at least about 50% reduction in pDCs in the subject at about 5 minutes, at about 10 minutes, about 15 minutes, about 30 minutes, about 1 hour, about 2 hours, about 3 hours, about 6 hours, about 12 hours, about 24 hours, or about 48 hours following administration of the anti-ILT7 therapy. In specific embodiments, a subject who has been administered a therapeutically effective amount of the anti-ILT7 therapy described herein shows a reduction in pDCs of greater than 50% at about 24 hours following administration of the anti-ILT7 therapy, compared to pDCs in the subject prior to administration of the anti-ILT7 therapy.

In certain embodiments, the reduction in pDCs persists for at least about 1 day, at least about 2 days, at least about 3 days, at least about 4 days, at least about 5 days, at least about 6 days, at least about 7 days, at least about 14 days, at least about 21 days, at least about 28 days, at least about 30 days, at least about 45 days, at least about 60 days, at least about 90 days, or at least about 180 days following administration of a therapeutically effective amount of the anti-ILT7 therapy described herein to a subject in need thereof. In some aspects, the reduction in pDCs persists for at least about 30 days following administration of a therapeutically effective amount of the anti-ILT7 therapy described herein to a subject in need thereof. In additional aspects, the reduction in pDCs persists for at least about 60 days following administration of a therapeutically effective amount of the anti-ILT7 therapy described herein to a subject in need thereof.

In specific embodiments, the VIB7734 is administered to the subject in a dose of from about 0.1 mg/dose to about 1000 mg/dose. In more specific embodiments, the VIB7734 is administered in a dose of about 1 mg/dose, about 5 mg/dose, about 15 mg/dose, about 50 mg/dose, about 100 mg/dose, about 125 mg/dose, about 150 mg/dose, about 175 mg/dose, about 200 mg/dose, about 225 mg/dose, about 250 mg/dose, about 275 mg/dose or about 300 mg/dose. In one embodiment, in any method disclosed herein, the VIB7734 is administered at a dose of about 150 mg/dose.

In additional embodiments, the anti-T1i therapies described herein are co-administered with at least one additional therapy selected from the group consisting of remdesivir, chloroquine, hydroxychloroquine, a corticosteroid, an interleukin-6 (IL-6) inhibitor, an interleukin-2 (IL-2) inhibitor, a plasma transfusion and a j anus kinase (JAK) inhibitor. The term co-administer as used herein means that the pharmacological activity of the two therapies may overlap. Co-administration can thus include embodiments in which two or more distinct therapies are administered simultaneously or it can also mean that two or more distinct therapies are administered sequentially in time. The order of administration of the two or more therapies can be in any order. In one specific embodiment, the anti-T1i therapy is the second, third or even fourth therapy administered to the subject.

A "therapeutically effective amount," or "pharmaceutically effective amount," or "effective amount" of a compound (e.g., an anti-ILT7 therapy of the disclosure) refers to an amount that is sufficient to produce a desired prophylactic, therapeutic or ameliorative response in a subject, or an amount that is sufficient to result in prevention or amelioration of one or more symptoms of a disease or condition in a statistically significant manner. When referring to an individual active ingredient administered alone, a therapeutically effective dose refers to that ingredient alone. When referring to a combination, a therapeutically effective dose refers to combined amounts of the active ingredients that result in the therapeutic effect, whether administered serially or simultaneously. As used herein, the term "therapeutically effective amount" means that the anti-ILT7 therapies of the disclosure are able to exert a statistically significant medically beneficial effect when used as prescribed or directed, as compared to a placebo. The therapeutically effective amount will vary depending upon the species and weight of the subject to be administered, but may be ascertained using standard techniques. In certain embodiments, a therapeutically effective amount of an anti-ILT7 therapy of the disclosure ranges from about 0.1 mg to about 1000 mg. In other embodiments, a therapeutically effective amount of an anti-ILT7 therapy of the disclosure ranges from about 50 mg to about 150 mg. In certain aspects, a therapeutically effective amount of an anti-ILT7 therapy of the disclosure includes, but is not limited to, about 1 mg, about 5 mg, about 15 mg, about 50 mg, about 100 mg, about 150 mg, about 300 mg, about 500 mg, or about 1000 mg. A therapeutically effective amount of an anti-ILT7 therapy of the disclosure may be administered to a subject in need thereof in a single dose or in multiple doses.

Therefore, in some embodiments, a therapeutically effective amount of the anti-T1i, such as but not limited to VIB7734, therapy described herein is administered to a subject in need thereof at least once every month. In other embodiments, a therapeutically effective amount of the anti-ILT7 therapy described herein is administered to the subject at least once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46, 47, 48, 49, 50, 51, or 52 weeks. In other embodiments, a therapeutically effective amount of the anti-T1i therapy described herein is administered to the subject at least once about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46, 47, 48, 49, 50, 51, or 52 days. In some embodiments, a therapeutically effective amount of the anti-T1i therapy described herein is administered to the subject at least once about every 4 weeks. In additional embodiments, a therapeutically effective amount of the anti-T1i therapy described herein is administered to the subject at least once about every 8 weeks or at least once about every 12 weeks. In further embodiments, a therapeutically effective amount of the anti-T1i therapy described herein is administered to the subject at least once about every two or three months. In still further embodiments, a therapeutically effective amount of the anti-T1i therapy described herein is administered to the subject at least once about every year or at least once about every 2 years.

In some embodiments, the respiratory virus is selected from the group consisting of rhinovirus, adenovirus, influenza virus, respiratory syncytial virus, enterovirus D68, Severe Acute Respiratory Syndrome-Coronoavirus (SARS-CoV), Middle Eastern Respiratory Syndrome-coronavirus (MERS-CoV) and Severe Acute Respiratory Syndrome-coronavirus-2 (SARS-CoV-2). In certain embodiments, the anti-T1i therapy is administered to the subject after the subject has developed at least one symptom of an exaggerated immune response. In some embodiments, the at least one symptom an exaggerated immune response is selected from the group consisting of increased circulating levels of pro-inflammatory cytokines, increased local levels of pro-inflammatory cytokines, T-cell lymphopenia and increased inflammatory markers.

In some embodiments, the anti-T1i therapy is administered to the subject before the subject has developed at least one symptom of an exaggerated immune response. In particular embodiments, the subject is a high-risk subject. In some embodiments, the high-risk subject is a subject that is at least 60 years old, has a pre-existing respiratory condition or is immunocompromised. In some embodiments, the anti-T1i therapy is administered to the subject after the subject exhibits at least one clinical marker of IMPI.

In some embodiments, the at least one clinical marker of IMPI is selected from the group consisting of shortness of breath, hypoxia, abnormal chest imaging and transaminitis. In certain embodiments, the anti-T1i therapy is an antibody or antibody fragment that binds to immunoglobulin-like transcript 7 (ILT7) protein present on plasmacytoid dendritic cells (pDCs). In particular embodiments, the anti-ILT7 antibody or antibody fragment is VIB7734 antibody or a fragment thereof.

In some embodiments, administration of VIB7734 or a fragment thereof depletes levels of circulating pDCs or depletes levels of respiratory pDCs, thereby reducing the activity, function or production of T1i in the subject. In certain embodiments, administration of VIB7734 or a fragment thereof depletes levels of circulating pDCs or depletes levels of respiratory pDCs by inducing antibody-dependent cell-mediated cytotoxicity (ADCC) of the circulating pDCs or the respiratory pDCs. In particular embodiments, the depletion in the levels of circulating pDCs or respiratory pDCs is reversible.

In some embodiments, the VIB7734 is administered in a dose of from about 0.1 mg/dose to about 1000 mg/dose. In some embodiments, the VIB7734 is administered in a dose of about 1 mg/dose, about 5 mg/dose, about 15 mg/dose, about 50 mg/dose, about 100 mg/dose, or about 150 mg/dose. In particular embodiments, the VIB7734 is administered by subcutaneous injection.

In some embodiments, the anti-T1i therapy is an antibody or antibody fragment that binds to interferon α/β receptor (IFNAR), thereby reducing the activity, function or production of T1i in the subject. In particular embodiments, the anti-IFNAR antibody or antibody fragment is anifrolumab or a fragment thereof. In certain embodiments, the anti-T1i therapy is an antibody or antibody fragment that binds to α-interferon (αIFN), thereby reducing the activity, function or production of T1i in the subject. In some embodiments, the anti-αIFN antibody or antibody fragment is sifalimumab or a fragment thereof.

In some embodiments, the anti-T1i therapy is co-administered at least one therapy selected from the group consisting of remdesivir, chloroquine, hydroxychloroquine, a corticosteroid, an interleukin-6 (IL-6) inhibitor, an interleukin-2 (IL-2) inhibitor, a plasma transfusion and a j anus kinase (JAK) inhibitor.

In some embodiments, the Type 1 interferon is interferon-α (IFNα).

The present disclosure relates to methods for treating or preventing immune-mediated pulmonary injury (IMPI) in a subject in need thereof, the method comprising administering to the subject an antibody or antibody fragment that binds to immunoglobulin-like transcript 7 (ILT7) protein.

In some embodiments, the anti-ILT7 antibody or antibody fragment is VIB7734 or a fragment thereof. In certain embodiments, administration of VIB7734 or a fragment thereof depletes levels of circulating pDCs or depletes levels of respiratory pDCs, thereby reducing the activity, function or production of T1i in the subject. In some embodiments, administration of VIB7734 or a fragment thereof depletes levels of circulating pDCs or depletes levels of respiratory pDCs by inducing antibody-dependent cell-mediated cytotoxicity (ADCC) of the circulating pDCs or the respiratory pDCs. In certain embodiments, the depletion in the levels of circulating pDCs or respiratory pDCs is reversible.

In some embodiments, VIB7734 is administered at a dose of from about 0.1 mg/dose to about 1000 mg/dose. In some embodiments, VIB7734 is administered at a dose of about 1 mg/dose, about 5 mg/dose, about 15 mg/dose, about 50 mg/dose, about 100 mg/dose, or about 150 mg/dose. In certain embodiments, VIB7734 is administered at a dose of about 150 mg/dose.

In some embodiments, VIB7734 is administered by subcutaneous injection.

In some embodiments, the respiratory virus is selected from the group consisting of rhinovirus, adenovirus, influenza virus, respiratory syncytial virus, enterovirus D68, Severe Acute Respiratory Syndrome-Coronoavirus (SARS-CoV), Middle Eastern Respiratory Syndrome-coronavirus (MERS-CoV) and Severe Acute Respiratory Syndrome-coronavirus-2 (SARS-CoV-2).

The present disclosure relates to methods for treating a subject infected with Severe Acute Respiratory Syndrome-coronavirus-2 (SARS-CoV-2), the method comprising administering to the subject an antibody or antibody fragment that binds to immunoglobulin-like transcript 7 (ILT7) protein, wherein the antibody or antibody fragment that binds to ILT7 is administered to the subject.

In some embodiments, the anti-ILT7 antibody or antibody fragment is VIB7734 or a fragment thereof. In certain embodiments, administration of VIB7734 or a fragment thereof depletes levels of circulating pDCs or depletes levels of respiratory pDCs, thereby reducing the activity, function or production of T1i in the subject. In some embodiments, administration of VIB7734 or a fragment thereof depletes levels of circulating pDCs or depletes levels of respiratory pDCs by inducing antibody-dependent cell-mediated cytotoxicity (ADCC) of the circulating pDCs or the respiratory pDCs. In some embodiments, the depletion in the levels of circulating pDCs or respiratory pDCs is reversible.

In some embodiments, VIB7734 is administered at a dose of from about 0.1 mg/dose to about 1000 mg/dose. In certain embodiments, VIB7734 is administered at a dose of about 1 mg/dose, about 5 mg/dose, about 15 mg/dose, about 50 mg/dose, about 100 mg/dose, or about 150 mg/dose. In particular embodiments, VIB7734 is administered at a dose of about 150 mg/dose. In some embodiments, VIB7734 is administered by subcutaneous injection.

In some embodiments, a pharmaceutical composition comprising one of the anti-T1i therapies used in the methods of the present disclosure will include pharmaceutically acceptable carriers, diluents, or excipients. In this regard, "pharmaceutically acceptable carriers, diluents, or excipients" include but are not limited to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that may or may not have been approved by the United States Food and Drug Administration as being acceptable for use in humans or domestic animals. For example, appropriate carriers are known to those skilled in the art and include stabilizers, diluents, and buffers. Suitable stabilizers include carbohydrates, such as sorbitol, lactose, mannitol, starch, sucrose, dextran, and glucose, and proteins, such as albumin or casein. Suitable diluents include saline, Hanks Balanced Salts, and Ringers solution. Suitable buffers include an alkali metal phosphate, an alkali metal carbonate, or an alkaline earth metal carbonate.

In certain aspects, the pharmaceutical compositions used in the methods of the disclosure may further contain one or more auxiliary substance, such one or more lipids, phospholipids, carbohydrates, and lipopolysaccharides. In some embodiments, pharmaceutical compositions used in the methods of the disclosure optionally comprise one or more additional active substances.

In certain cases, the pharmaceutical compositions used in the methods of the disclosure can be prepared by techniques known to those skilled in the art. General considerations in the formulation and/or manufacture of pharmaceutical compositions may be found, for example, in Remington: The Science and Practice of Pharmacy 21st ed., Lippincott Williams & Wilkins, 2005 (incorporated herein by reference in its entirety). Generally, an anti-ILT7 therapy used in the methods of the disclosure is mixed with a carrier to form a solution, suspension, or emulsion. One or more of the additives discussed herein may be added in the carrier or may be added subsequently. The pharmaceutical compositions used in the methods of the disclosure may be an aqueous solution, emulsion or suspension or may be a dried preparation. In certain aspects, the pharmaceutical compositions used in the methods of the disclosure may be desiccated or lyophilized, for example, by freeze drying or spray drying for storage or formulations purposes. They may be subsequently reconstituted into liquid compositions by the addition of an appropriate liquid carrier or administered in dry formulation using methods known to those skilled in the art.

The choice of administration of the pharmaceutical composition will depend on the formulation that is selected. The pharmaceutical compositions used in the methods of the disclosure are administered in a manner compatible with the dosage formulation, and in such amount as will be therapeutically effective. In certain aspects, a pharmaceutical composition used in the methods of the disclosure is formulated into preparations in solid, semi-solid, liquid or gaseous forms, including, but not limited to, tablets, capsules, powders, granules, ointments, solutions, suppositories, injections, inhalants, gels, microspheres, and aerosols.

In certain instances, a pharmaceutical composition comprising an anti-T1i therapy used in the methods of the disclosure may be in the form of a solid or liquid. In some aspects, the carrier(s) are particulate so that the compositions are, for example, in tablet or powder form. In other aspects, the carrier(s) are liquid, with a composition being, for example, an oral syrup, injectable liquid or an aerosol, which is useful in, for example, inhalatory administration. When intended for oral administration, a pharmaceutical composition comprising an anti-T1i therapy used in the methods of the disclosure is in either solid or liquid form, where semi-solid, semi-liquid, suspension and gel forms are included within the forms considered herein as either solid or liquid.

In certain aspects, as a solid composition for oral administration, a pharmaceutical composition comprising an anti-T1i therapy used in the methods of the disclosure may be formulated into a powder, granule, compressed tablet, pill, capsule, chewing gum, wafer or the like form. In some instances, such a solid composition will typically contain one or more inert diluents or edible carriers. In certain embodiments, one or more of the following may be additionally present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

These compositions can take the form of microspheres, solutions, suspensions, tablets, pills, capsules, sustained release formulations or powders and contain from about 0.001% to about 95% of an anti-T1i therapy used in the methods of the disclosure.

In some aspects, when a pharmaceutical composition of the disclosure is in the form of a capsule, for example, a gelatin capsule, it may contain, in addition to materials disclosed herein, a liquid carrier such as polyethylene glycol or oil. Oral formulations may also include normally employed incipients such as, for example, pharmaceutical grades of saccharine, cellulose and magnesium carbonate.

In other aspects, a pharmaceutical composition used in the methods of the disclosure is in the form of a liquid, for example, an elixir, syrup, solution, emulsion or suspension. In certain embodiments, the liquid may be for oral administration or for delivery by injection. In certain embodiments, when intended for oral administration, the pharmaceutical compositions used in the methods of the disclosure contain, one or more of a sweetening agent, preservatives, dye/colorant and flavor enhancer. In certain aspects, in a pharmaceutical composition intended to be administered by injection, one or more of a surfactant, preservative, wetting agent, dispersing agent, suspending agent, buffer, stabilizer and isotonic agent may be included.

In certain cases, liquid pharmaceutical compositions comprising an anti-T1i therapy used in the methods of the disclosure, whether they be solutions, suspensions or other like form, may include one or more of the following components: sterile diluents such as water for injection, saline solution, e.g., physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In some cases, the preparation can be enclosed in ampoules, disposable syringes or multiple dose vials made of glass or plastic. In some embodiments, an injectable pharmaceutical composition is preferably sterile.

In other embodiments, a pharmaceutical composition comprising an anti-T1i therapy used in the methods of the disclosure may be intended for topical administration, in which case the carrier may suitably comprise a solution, emulsion, ointment or gel base. In certain aspects, the base, for example, may comprise one or more of the following: petrolatum, lanolin, polyethylene glycols, bee wax, mineral oil, diluents such as water and alcohol, and emulsifiers and stabilizers. In other aspects, thickening agents may be present in a pharmaceutical composition for topical administration. In certain embodiments, if intended for transdermal administration, a pharmaceutical composition of an anti-T1i therapy used in the methods of the disclosure may be included with a transdermal patch or iontophoresis device.

In yet other embodiments, the pharmaceutical composition comprising an anti-T1i therapy used in the methods of the disclosure is intended for rectal administration, in the form, for example, of a suppository. For suppositories, binders and carriers may include, for example, polyalkalene glycols or triglycerides. In certain instances, a composition for rectal administration contains an oleaginous base as a suitable nonirritating excipient. Such bases include, without limitation, lanolin, cocoa butter or polyethylene glycol.

In other aspects, a pharmaceutical composition comprising an anti-T1i therapy used in the methods of the disclosure comprises dosage units that can be administered as an aerosol. The term aerosol is used to denote a variety of systems ranging from those of colloidal nature to systems consisting of pressurized packages. In certain embodiments, delivery is accomplished by a liquefied or compressed gas or by a suitable pump system that dispenses the active ingredients. In some embodiments, aerosols of an anti-T1i therapy used in the methods of the disclosure may be delivered in single phase, bi-phasic, or tri-phasic systems in order to deliver the active ingredient(s). In other embodiments, delivery of the aerosol includes the necessary container, activators, valves, subcontainers, and the like, which together may form a kit. One skilled in the art can readily determine specific aerosol formulations and delivery modes.

Pharmaceutical compositions of the disclosure may be administered in a suitable, nontoxic pharmaceutical carrier, may be comprised in microcapsules, microbeads, and/or may be comprised in a sustained release implant.

In some aspects, pharmaceutical compositions used in the methods of the disclosure include materials that form a coating shell around the active ingredients. In some instances, the materials that form the coating shell are typically inert, and may be selected from, for example, sugar, shellac, and other enteric coating agents.

In yet other aspects, the pharmaceutical compositions used in the methods of the disclosure in solid or liquid form include an agent that binds to an anti-T1i therapy described herein and thereby assist in the delivery of the anti-T1i therapy used in the methods of the disclosure. In certain cases, suitable agents that act in this capacity include a protein or a liposome.

In certain aspects, pharmaceutical compositions that will be administered to a subject take the form of one or more dosage units, where, for example, a tablet may be a single dosage unit, and a container of an anti-T1i therapy of the disclosure in aerosol form may hold a plurality of dosage units. Actual methods of preparing such dosage forms are known, or will be apparent to those skilled in this art; for example, see Remington: The Science and Practice of Pharmacy, 20th Edition (Philadelphia College of Pharmacy and Science, 2000). A composition to be administered will, in any event, contain a therapeutically effective amount of an anti-T1i therapy of the disclosure, or a pharmaceutically acceptable salt thereof, to aid in treatment of a disease or condition of interest in accordance with the teachings herein.

In specific embodiments, a pharmaceutical composition of the disclosure comprises about 100 mg/mL of VIB7734, about 20 mM histidine, about 240 mM sucrose, and about 0.02% polysorbate 80, wherein the composition has a pH of about 6.0.

Pharmaceutical compositions used in the methods of the disclosure may desirably be administered at several intervals in order to sustain therapeutic levels. Pharmaceutical compositions of the disclosure may be used in conjunction with other bacteriocidal or bacteriostatic methods.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

All publications, patent applications, patents, and other references mentioned herein are expressly incorporated by reference in their entirety. The materials, methods, and examples described herein are illustrative only and are not intended to be limiting.

EXAMPLES

In autoimmune diseases, upon activation by immune complexes to self-nucleic acids, plasmacytoid dendritic cells (pDCs) secrete significant amounts of type I and type III interferons (IFNs). pDCs constitute about 0.4% of circulating white blood cells and can recognize viral nucleic acids, which are often bound to other proteins or to immunoglobulins. Although this response is believed to contribute to antiviral defense, evidence has accumulated that pDCs and type I IFNs also contribute to the pathogenesis of numerous autoimmune diseases. Type I IFN levels cannot be directly measured in a reliable way; however, binding of type I IFN to its receptor leads to local and systemic upregulation of type I IFN-inducible genes. The messenger ribonucleic acid (mRNA) levels of these type I IFN-inducible genes can be measured in blood and analyzed as a composite outcome referred to as the "type I interferon gene signature" (IF-NGS).

A Phase 1, randomized, site-blinded/sponsor-unblinded, placebo-controlled trial of a single escalating subcutaneous dose of VIB7734 was carried out in 5 successive cohorts of patients with systemic lupus erythematosus (SLE), Sjögren's syndrome (SS), dermatomyositis (DM), polymyositis (PM), or systemic sclerosis (SSc). The trial evaluated the safety, drug levels, pDC levels, anti-drug antibodies, and impact on a 21-gene type I IFN gene signature of VIB7734.

All data were presented in the form of listings sorted by cohort, treatment, and subject number. Tabular summaries of the data collected were presented by treatment group. Categorical data was summarized by the frequency counts and percentage of subjects in each category. Percentages were calculated based on non-missing observations where applicable. Continuous variables were summarized by descriptive statistics including number of observations, mean, standard deviation, median, minimum, and maximum. In general, unless stated otherwise, "baseline" was defined as the last value prior to first dose of investigational product.

Example 1: Study Design

A total of 36 subjects were enrolled in the study. The enrolled subjects had the following diagnoses: SLE 19 (53%), SS 16 (44%), SSc 3 (8%), PM 2 (6%), and DM 2 (6%). Baseline demographic characteristics were well-balanced and generally similar between the total VIB7734 group and the placebo group. The majority of the subjects were White and were females (32 [88.9%]). The enrolled subjects were randomized in a 3:1 ratio within 5 cohorts to receive a single subcutaneous dose of VIB7734 or matching placebo as follows:

Cohort 1: 1 mg VIB7734 (n=3) or placebo (n=1);
Cohort 2: 5 mg VIB7734 (n=6) or placebo (n=2);
Cohort 3: 15 mg VIB7734 (n=6) or placebo (n=2);
Cohort 4: 50 mg VIB7734 (n=6) or placebo (n=2);
Cohort 5: 150 mg VIB7734 (n=6) or placebo (n=2).

Figure 2:
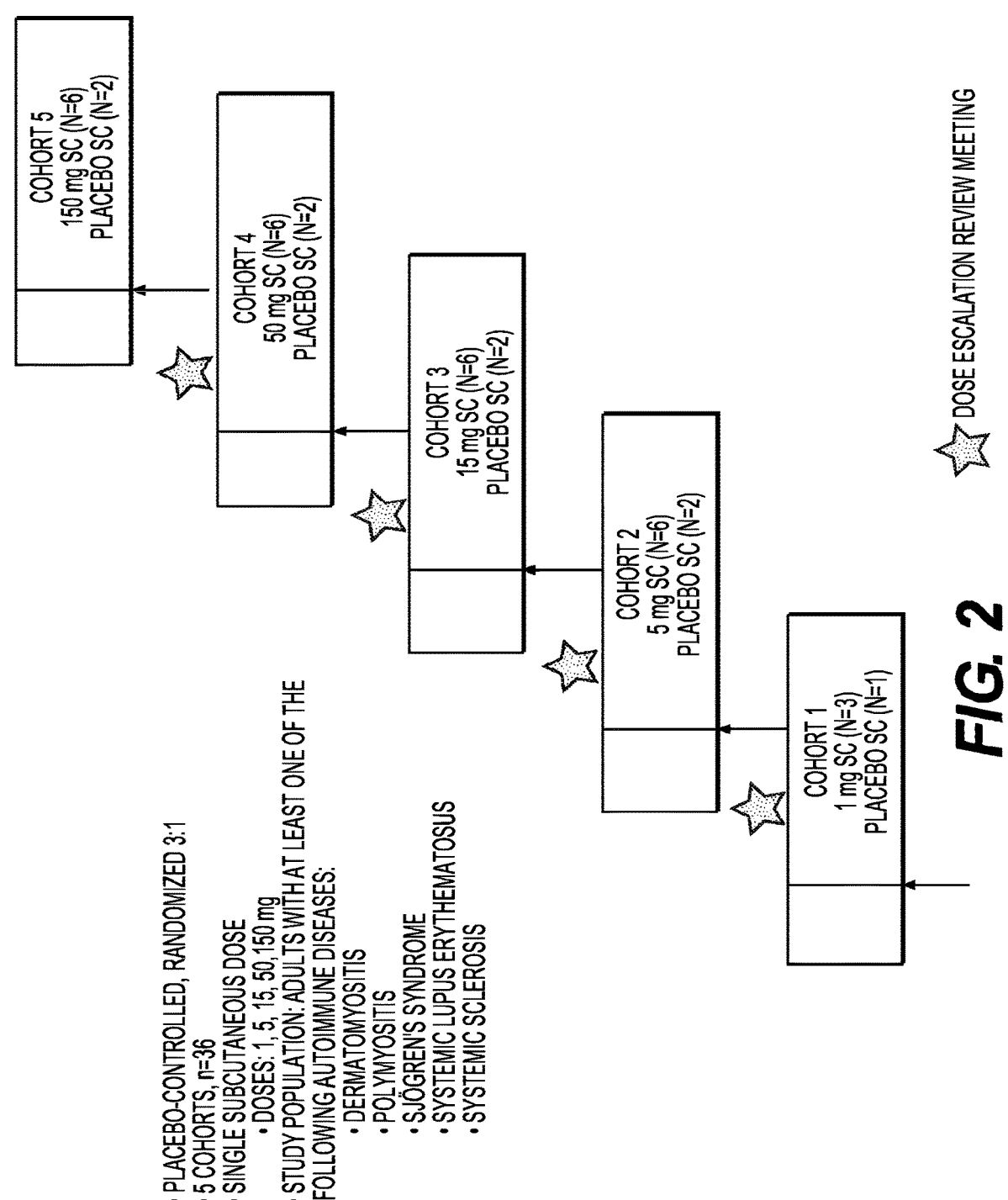
FIG. 2 shows details of the single ascending dose study design.

A diagrammatic presentation of the study is provided in FIGS. 1 and 2. A screening visit was performed within 42 days prior to dosing. Subjects received VIB7734 on Day 1 and were observed overnight (in the facility) for any safety concerns. Subjects were discharged on Day 2 after completion of all study procedures and ensuring that there were no safety issues. This was followed by a treatment follow-up period of 85 days. During this period, subjects returned to the study site on Days 4, 8, 15, 29, 57, and 85. The subjects were evaluated for pDC repletion. The pDC repletion criteria was met if pDC level was ≥50% of the subject's baseline value or pDC level was greater than the lower limit of the standard range as defined in the laboratory manual. If they did not meet the pDC repletion criteria at Day 85, they were to be followed up for additional 252 days (to study Day 337). If the pDC repletion criteria was not met by the Day 337 visit, the medical monitor in consultation with the investigator determined the need for further follow-up.

Subjects received only one dose of investigational product during the study. As shown in FIG. 2, cohorts were enrolled in a dose-escalating manner to provide time for review of safety and tolerability data before progressing to the next dose level (cohort). The decision to escalate to the next dosing cohort was made by the Dose Escalation Committee (DEC).

In each cohort, there was at least a 48 hour interval between the dosing of first and second subjects and between the second and the third subject. Starting with the third subject in each cohort, there was at least a 24 hour interval between the dosing of subsequent subjects. Dosing for Cohorts 2, 3, 4, and 5 commenced once all subjects in the previous cohort had been randomized and administered with VIB7734, all evaluable subjects had completed at least the Day 15 visit (Visit 6), and the cumulative safety data of all exposed subjects was reviewed by the DEC, who agreed the safety profile to be acceptable.

Example 2: Evaluation of Adverse Reactions

Serious adverse events occurred in 1 subject in the VIB7734 15 mg group (colitis) and 1 subject in the placebo group (death due to cerebral hemorrhage). At least one adverse event (AE) was reported in 69% of VIB7734-treated, and 80% of placebo-treated subjects. The most commonly reported AEs in VIB7734-treated subjects were diarrhea (12%) and upper respiratory tract infection (12%). No injection site reactions or hypersensitivity reactions occurred.

Example 3: Immunogenicity Evaluations

Blood samples were collected on Days 1, 2, 4, 8, 15, 29, 57, and 85 to evaluate anti-drug antibody (ADA) response to VIB7734 in human serum. These evaluations were performed utilizing a validated electrochemiluminescence immunoassay method for the detection, and confirmation and titration of anti-drug antibodies to VIB7734 in human serum. Samples found to be negative in the screening tier were reported to have a titer of <30.

Baseline and post-baseline ADA results were recorded for all 26 subjects in the VIB7734 group and 9 subjects in placebo group. No positive results were observed in either treatment groups. No incidence of ADA persistent positive or transient positive was observed in either treatment groups. Thus, overall, for subcutaneous injection of VIB7734 in doses ranging from 1 to 150 mg, no safety, tolerability, or immunogenicity issues were identified.

Example 4: Pharmacokinetic Evaluations

Blood samples were collected on Days 1, 2, 4, 8, 15, 29, 57, and 85 to evaluate PK of VIB7734 in serum. Concentrations of VIB7734 were measured in human serum samples by utilizing a validated enzyme-linked immunosorbent assay (ELISA) immunoassay method. The validated measurement range of the assay was 0.025 μg/mL to 25.60 μg/mL. Results below the lower limit of quantitation (LLOQ) were reported as <0.10 μg/mL.

The PK analysis was performed on time data of concentration of VIB7734 from all 26 subjects who received any dose of VIB7734. Mean serum concentration-time profiles of VIB7734 following a single subcutaneous dose of 1, 5, 15, 50, or 150 mg are shown in FIG. 3. Following the 1 mg dose, all concentrations were below the quantitation limit (BLQ), therefore all the summary PK parameters are based on 5-150 mg dose levels. PK exposures of VIB7734 increased approximately dose proportionally. After a single subcutaneous injection on Day 1, peak concentrations were observed in 5 to 8 days post dose. Exposures increased in an approximately dose-proportional manner with increasing dose levels. The estimated half-life ranged from 13 to 20 days across dose levels. Mean extravascular clearance ranged from 468 to 1030 mL/day. Mean extravascular volume of distribution ranged from 9.9 to 19.0 L.

Example 5: Pharmacodynamic Evaluations: pDC Levels

Whole blood samples for pDC levels were collected on Days 1, 2, 4, 8, 15, 29, 57, and 85. The baseline pDC level was defined as the mean of the levels measured at Visits 1 and 2. If the screening (Visit 1) sample was not drawn or failed for technical reasons, it was to be repeated and results had to be available before the subject could be randomized since the result was needed to determine that the subject met all inclusion/exclusion criteria. If the Day 1 (Visit 2) sample was not drawn or failed for technical reasons, the value from the Visit 1 sample was to be considered the baseline. The study site was blinded to post-baseline pDC levels.

The pDC levels were quantified in two ways during the study: 1) as a percentage of the CD45+ peripheral blood mononuclear cells (PBMCs, primary method), and 2) as a concentration of pDCs per μL (secondary method). The primary pDC measure is the pDCs as a % of CD45+ PBMCs since that is what is directly measured by the flow cytometry assay used in this study.

At baseline the mean pDC level in the blood was 0.13% (SD: 0.056%) of PBMCs in the VIB7734-treated subjects. The mean concentration of pDCs at baseline in the VIB7734-treated subjects was 2.53 cells/μL (SD: 1.24%). The levels and change from baseline in pDC (% of CD45+ cells) over time is presented in FIG. 4. The levels and change from baseline in absolute concentration of pDC over time is presented in FIG. 5. The changes in absolute pDC levels over time is presented in FIG. 6.

There was decrease in the blood levels of pDCs after SC administration of all tested doses of VIB7734. Median reductions of at least 50% in the pDC level of VIB7734-treated subjects were evident at 24 hours after dosing (the first blood draw done after dosing) in all VIB7734 treatment groups, with a maximal reduction of 90%. Increasing doses were associated with a non-linear increase in pDC reduction. At Day 15, median pDC levels changed as follows for the VIB7734-treated cohorts: 1 mg: −57%, 5 mg: −66%, 15 mg: −70%, 50 mg: −82%, and 150 mg: −90%, versus +7.5% for the placebo-treated group.

Figure 4:
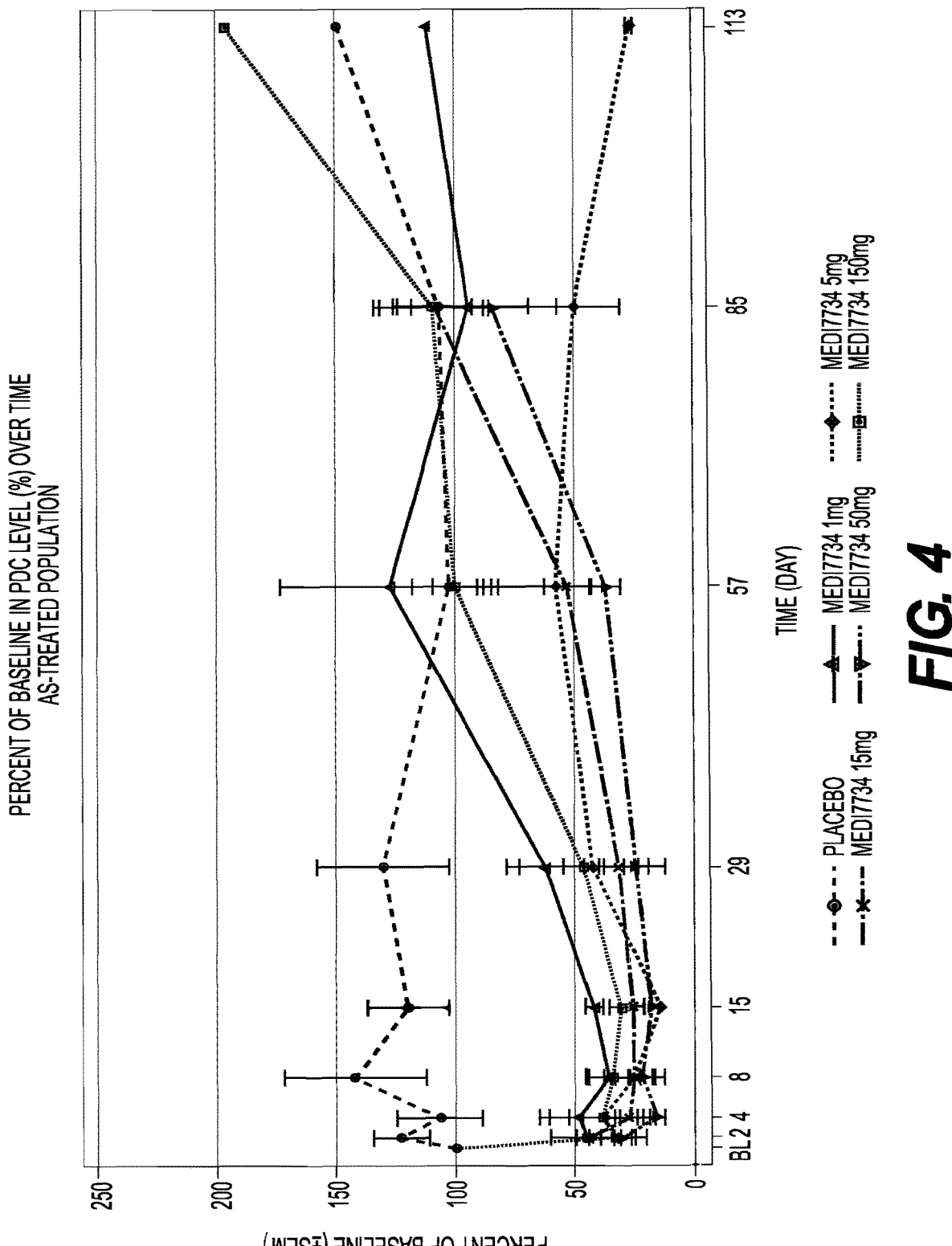
FIG. 4 shows pDC levels (%) over time, as a percent of the baseline level (value using % peripheral blood mononuclear cells) in a subject, suffering from at least one of the following five autoimmune diseases: SLE, Sjögren's syndrome, dermatomyositis, polymyositis, or systemic sclerosis, following a single subcutaneous dose (1 mg, 5 mg, 15 mg, 50 mg, or 150 mg) of an Anti-ILT7 therapy of the disclosure (VIB7734, also known as MEDI7734).
Figure 5:
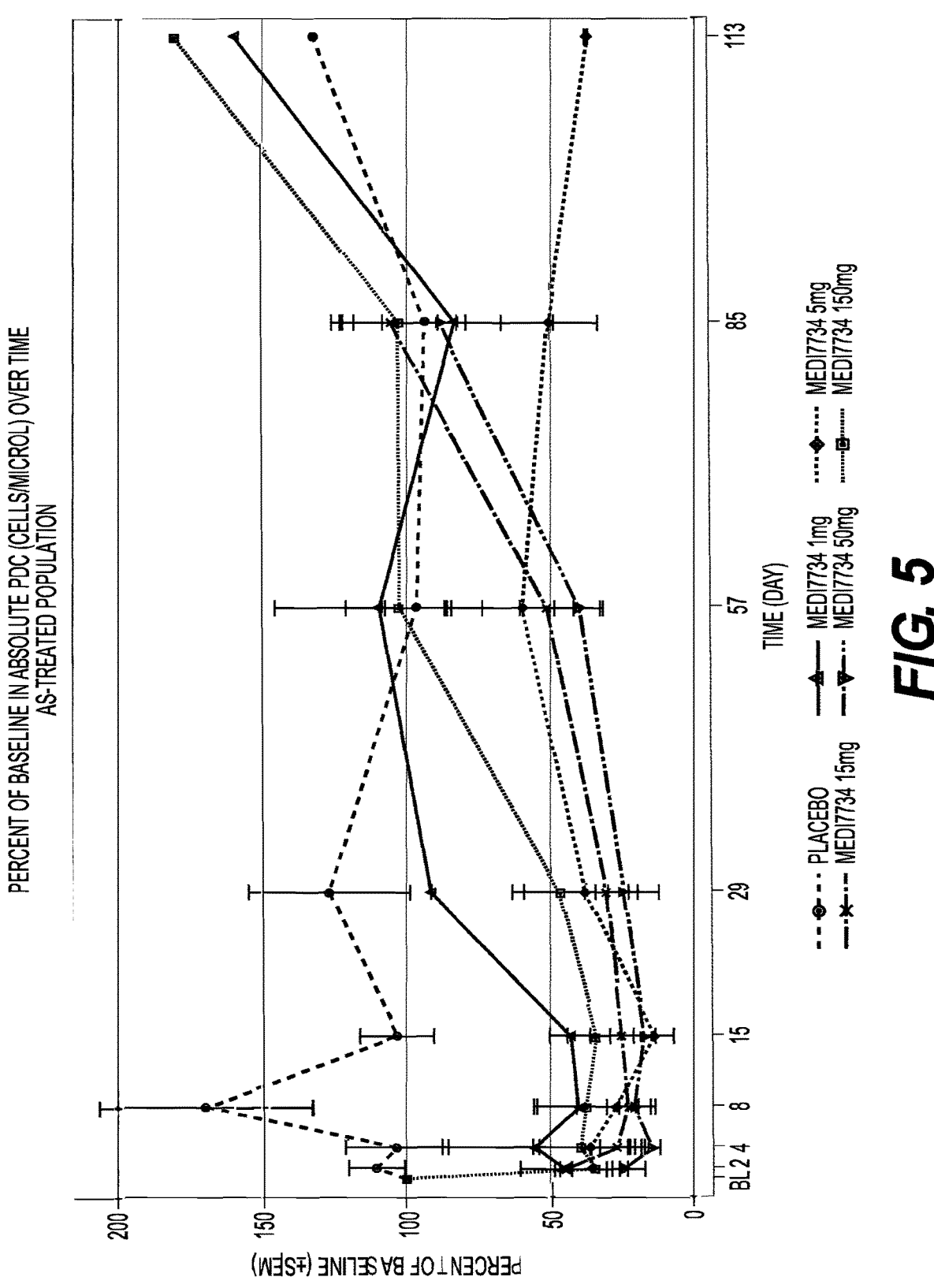
FIG. 5 shows pDC levels (%) over time, as a percent of the baseline level (value using absolute concentration) in a subject, suffering from at least one of the following five autoimmune diseases: SLE, Sjögren's syndrome, dermatomyositis, polymyositis, or systemic sclerosis, following a single subcutaneous dose (1 mg, 5 mg, 15 mg, 50 mg, or 150 mg) of an Anti-ILT7 therapy of the disclosure (VIB7734).
Figure 6:
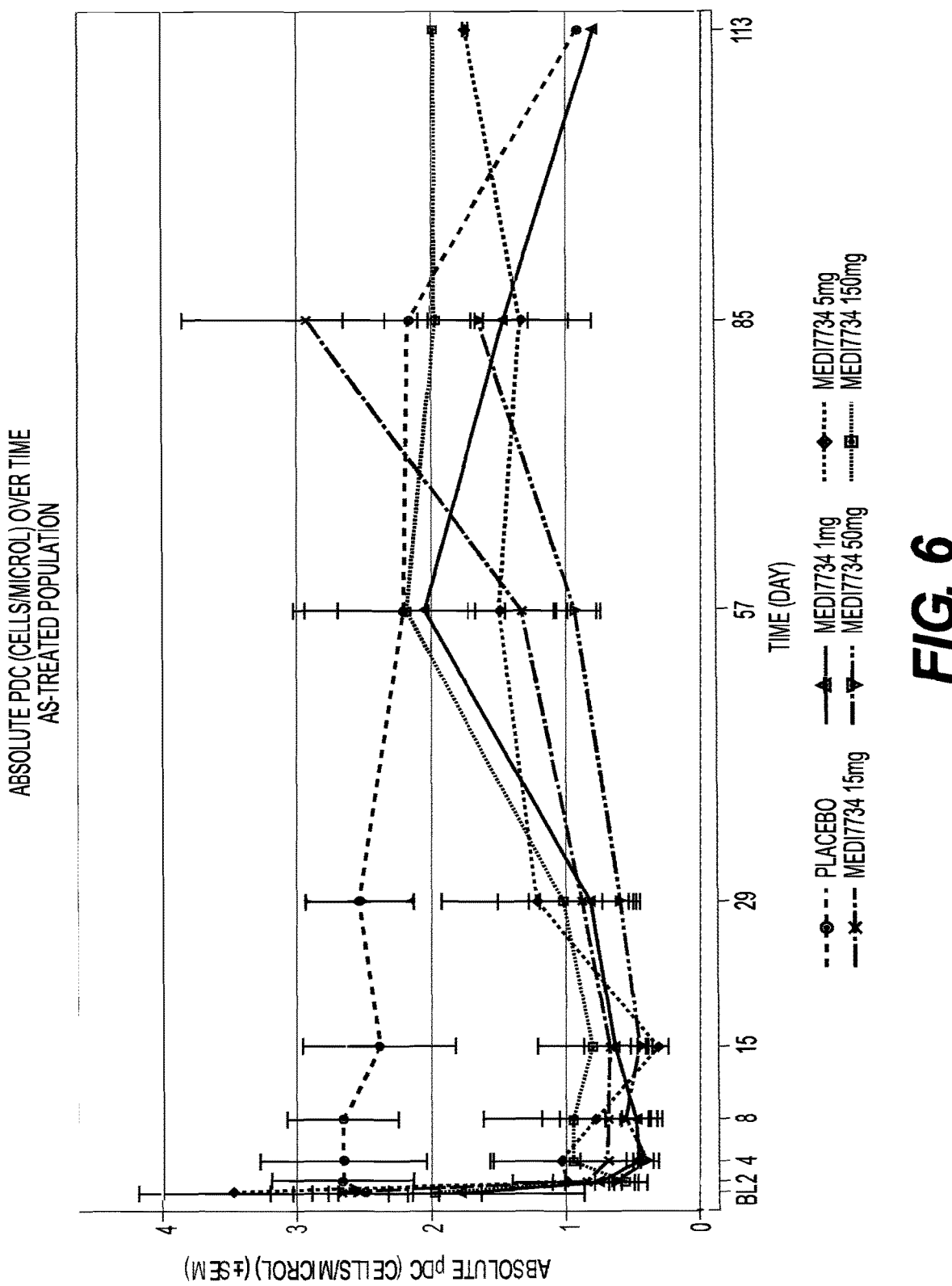
FIG. 6 shows pDC levels (absolute concentration; cells/microliter) in a subject, suffering from at least one of the following five autoimmune diseases: SLE, Sjögren's syndrome, dermatomyositis, polymyositis, or systemic sclerosis, following a single subcutaneous dose (1 mg, 5 mg, 15 mg, 50 mg, or 150 mg) of an Anti-ILT7 therapy of the disclosure (VIB7734).
Figure 8:
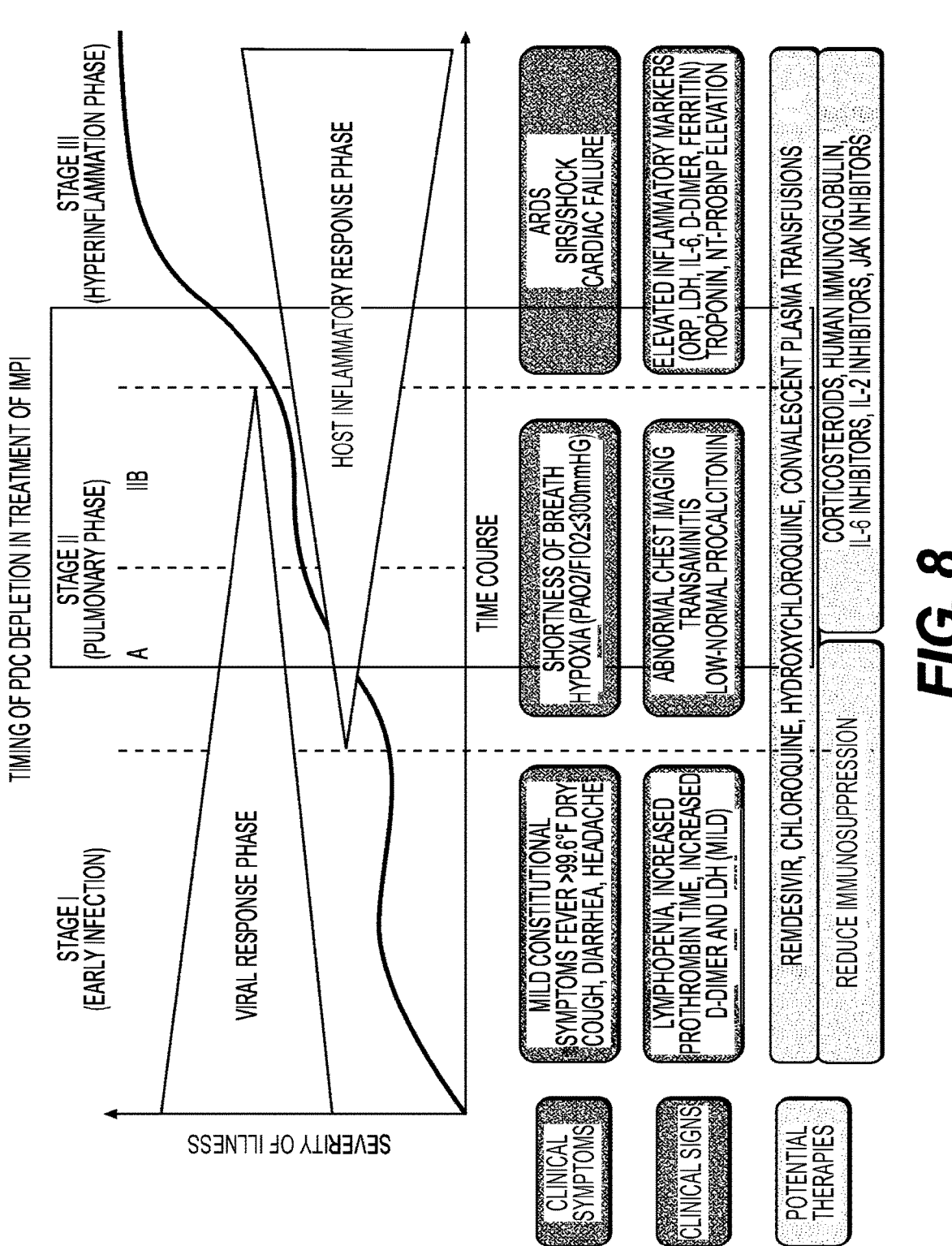
FIG. 8 shows the timing of potential maximal therapeutic benefit of the methods of treatment or prevention described herein during the course of development of IMPI.
Figure 11:
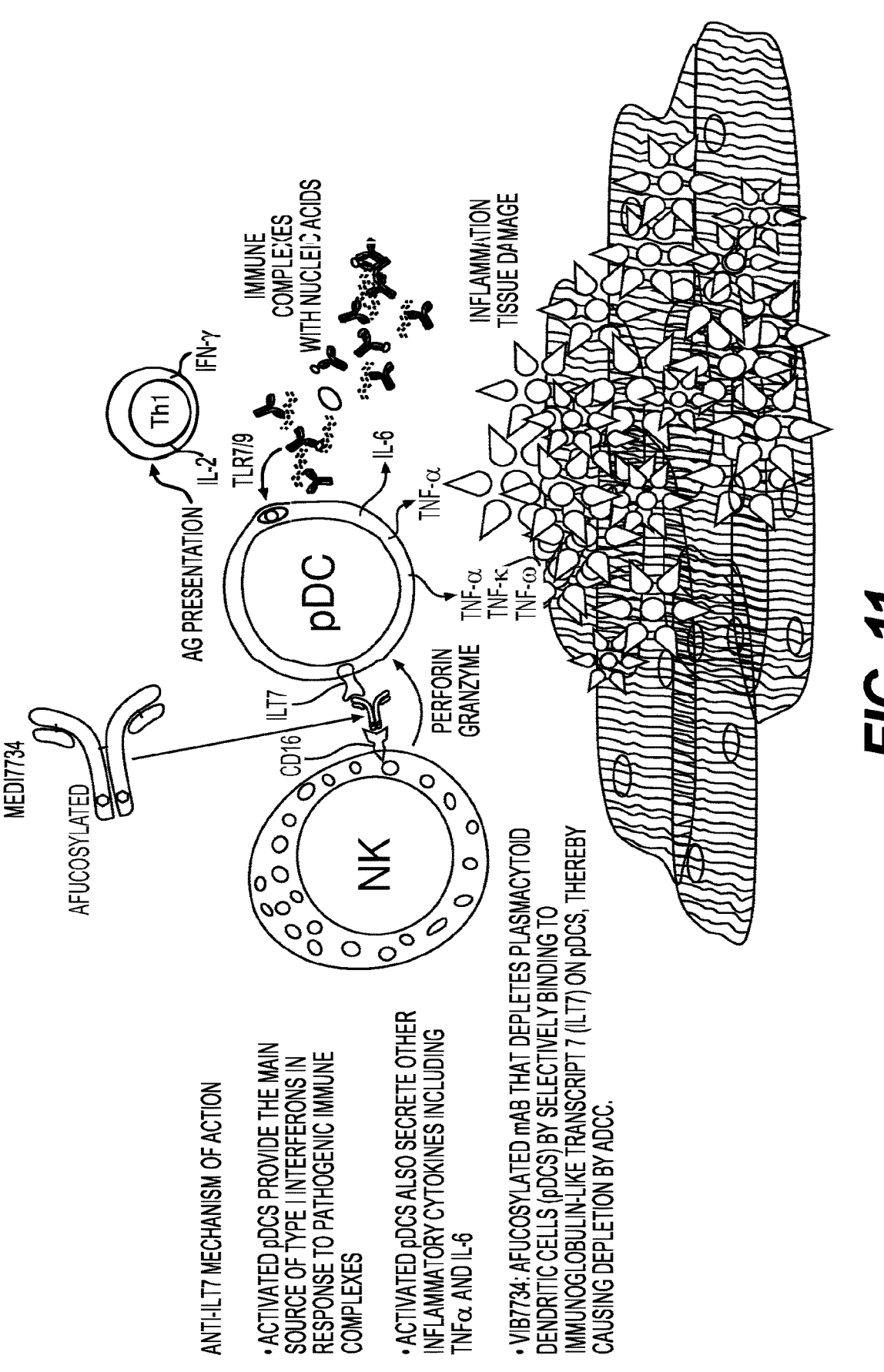
FIG. 11 shows the cascade of events in pDC induced tissue damage and how an anti-T1i therapy described here, e.g., VIB7734, can block, attenuate, inhibit or slow the progression of such damage.

Increasing doses were generally associated with a longer duration of pDC reduction. The effect was reversible in all cases. As shown in FIGS. 4-6, median pDC levels returned to above 50% of baseline at the following timepoints for each cohort: 1 mg: Day 29, 5 mg: Day 57, 15 mg: Day 57, 50 mg: Day 85, 150 mg: Day 113. Thus, subcutaneous injection of VIB7734 in doses ranging from 1 to 150 mg caused a reversible, dose-dependent reduction in circulating pDC levels.

The maximal degree of reduction from baseline of the median pDC level was −90%. The increase in the maximal depletion appears to nearly plateau at doses of 15 to 150 mg.

Figure 12:
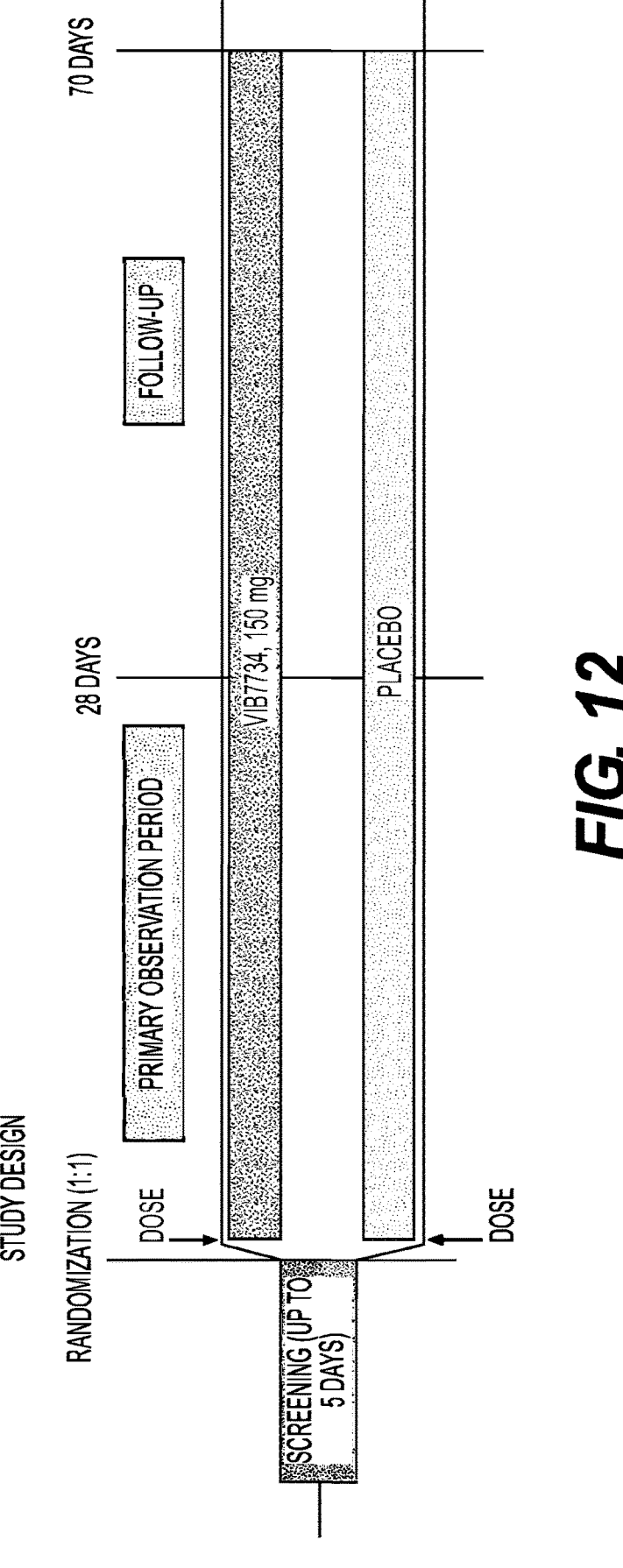
FIG. 12 shows the overall study design for a phase 1b randomized, double-blind, placebo-controlled study intended to assess the potential benefit and evaluate the safety and tolerability of a single subcutaneous (SC) dose of VIB7734 in hospitalized patients with documented infection of severe acute respiratory syndrome coronavirus 2 (SARS-CoV-2) with pulmonary involvement.

Example 6: Safety and Efficacy of VIB7734 for the Treatment and Prevention of Acute Lung Injury (ALI) in Patients with SARS CoV-2 Infection A randomized, double-blind, placebo-controlled study is performed to assess the potential benefit and evaluate the safety and tolerability of a single subcutaneous (SC) dose of VIB7734 in hospitalized patients with documented infection of severe acute respiratory syndrome coronavirus 2 (SARS CoV-2) with pulmonary involvement. The study consists of screening, a 28-day primary observation period, and a 6-week (42 day) follow-up period (FIG. 12). Safety will be assessed for 10 weeks following dosing. The pharmacokinetics (PK), pharmacodynamics (PD), and immunogenicity of VIB7734 in patients with confirmed SARS-CoV-2 infections will also be assessed.

Approximately 48 patients are randomized to placebo or VIB7734 treatment in a 1:1 ratio. Efficacy will be assessed during the 28 days following a single administration of VIB7734 or placebo. Safety will be assessed for 70 days following dosing. Initial enrollment will begin with enrolling a block of 4 patients who will be randomized 1:1 to placebo or VIB7734. These first 4 patients will be closely monitored for the first 48 hours after study treatment administration, and their clinical course will be reviewed by the voting members of the independent Data and Safety Monitoring Committee (iDSMC) before the remaining patients may be dosed. Randomization of the remaining eligible patients will be initiated only if the safety-related data of the first cohort is deemed to be acceptable by the iDSMC. The iDSMC will continue to closely monitor the safety of patients through scheduled assessments during the conduct of the study. The detailed procedures of the iDSMC and its composition, and the stopping rules, will be specified in the iDSMC charter.

VIB7734 at 150 mg or placebo will be administered as SC injection on Day 1, and post baseline assessments will be conducted on Days 3, 5, 7, 10, 14, 21, and 28. If a subject is discharged before the Day 28 visit and an in-person follow up cannot be conducted, adverse events (AEs) should be assessed remotely at all follow-up timepoints. Safety laboratory assessments can be done locally for the Day 28 visit, if feasible, and could be omitted for the earlier follow-up visits.

A follow-up in-person visit or phone call will be performed approximately 14 and 42 days after the end of the primary observation period. The study duration for an individual patient will not exceed 12 weeks (approximately 84 days). The end of the study is defined as last patient, last follow-up visit/phone call.

Patients eligible for this study represent a target population with confirmed SARS CoV-2 infection who have evidence of lower respiratory tract involvement and signs of a hyperinflammatory reaction, and who are at high risk of progressing to severe respiratory failure (acute lung injury (ALI)) requiring respiratory support, which is associated with a high risk of mortality.

Patients must meet all of the following criteria:

Age ≥18 years at the time of screening.

Hospitalized with coronavirus disease 2019 (COVID-19) pneumonia confirmed by World Health Organization criteria (including positive result on a nucleic acid amplification test, such as reverse transcriptase-polymerase chain reaction of any specimen; respiratory, blood, urine, stool, or other bodily fluid) and evidenced by a new infiltrate on chest X-ray or computed tomography scan.

Oxygen saturation ≤94%.

Negative influenza test.

Lymphocyte counts <103/μL and the presence of at least one of the following markers of hyperinflammation within 2 days prior to investigational product (IP) administration:

Elevated high sensitivity C-reactive protein (hsCRP) >50 mg/L

Ferritin >500 ng/mL

Lactate dehydrogenase (LDH) >300 U/L

D-dimers >500 ng/mL

Females of childbearing potential who are sexually active with a nonsterilized male partner must use a highly effective method of contraception from signing the informed consent form (ICF), and must agree to continue using such precautions through the end of the study follow-up; cessation of contraception after this point should be discussed with a responsible physician. Highly effective methods of contraception include:

a. combined (estrogen and progestogen containing) hormonal contraception associated with inhibition of ovulation:

i. oral ii. intravaginal iii. transdermal b. progestogen-only hormonal contraception associated with inhibition of ovulation:

i. oral ii. injectable iii. implantable c. intrauterine device d. intrauterine hormone-releasing system e. bilateral tubal occlusion f. vasectomized partner g. sexual abstinence Sexual abstinence is considered a highly effective method only if it is the preferred and usual lifestyle of the subject and the subject agrees to refrain from heterosexual intercourse from signing the ICF through the end of the study follow-up. Periodic abstinence, the rhythm method, and the withdrawal method are not acceptable methods of contraception. A recommendation that the female partners (of childbearing potential) of male study participants should use a highly effective method of contraception other than a barrier method is made.

a. Females of childbearing potential are defined as those who are not surgically sterile (surgical sterilization includes bilateral tubal ligation, bilateral oophorectomy, or hysterectomy) or those who are not postmenopausal (defined as 12 months with no menses without an alternative medical cause).

b. Vasectomized partner is a highly effective birth control method provided that partner is the sole sexual partner of the woman of childbearing potential trial participant and that the vasectomized partner has received medical assessment of the surgical success.

Nonsterilized male subjects who are sexually active with a female partner of childbearing potential must use a condom with spermicide from Day 1 through the end of the study.

Ability to complete the study, including follow-up period.

Any of the following will exclude the patient from participation in the study:

Any condition that, in the opinion of the Investigator, would interfere with evaluation of the investigational product (IP)IP or interpretation of patient safety or study results.

Respiratory failure defined based on resource utilization requiring at least one of the following:

Endotracheal intubation and/or mechanical ventilation,

Non-invasive positive pressure ventilation (new or increased from pre COVID diagnosis baseline in patients with obstructive sleep apnea), Extracorporeal membrane oxygenation (ECMO), or Clinical diagnosis of respiratory failure (ie, clinical need for one of the preceding therapies, or need for preceding therapies but not able to be administered in setting of resource limitation).

In the opinion of the Investigator, progression to death is imminent and inevitable within the next 24 hours.

Valid Do Not Intubate (DNI) or Do Not Resuscitate (DNR) order.

History of allergy or hypersensitivity reaction to any component of VIB7734.

Participation in another clinical study with an investigational product within 4 weeks prior to Day 1 or within 5 half-lives of the VIB7734, whichever is longer. (Participation in COVID-19 antiviral or antimalarial trials may be permitted after discussion with the Medical Monitor).

Liver cirrhosis or liver failure.

Known human immunodeficiency virus infection.

Known hepatitis B or known hepatitis C infection in the absence of a history of curative therapy.

Known or suspect active or latent tuberculosis infection.

Active bacterial, fungal, viral, or other infection (besides COVID-19).

Severe herpes zoster infection within 3 months before enrollment.

Within 2 days prior to IP administration, any of the following:

a. Aspartate aminotransferase (AST) >5×upper limit of normal (ULN)

b. Alanine aminotransferase (ALT) >5×ULN c. Neutrophil count <500/μL (or <0.5×$10^{-9}$/L)

d. Platelet count <50000/μL (or <55×$10^{-9}$/L)

e. Hemoglobin <7 g/dL (or <70 g/L)

f. Total lymphocyte count <200 cells/mm$^3$ g. Estimated glomerular filtration rate <30 mL/min/1.73 m$^2$ Clinically significant cardiac disease within 6 months, including: unstable angina, myocardial infarction within 6 months, congestive heart failure, arrhythmia requiring acute therapy, and pulmonary arterial hypertension.

History of severely impaired respiratory function at baseline (not related to COVID-19) based on requirement for home oxygen of >4 L/min or based on other medical history known to the Investigator.

History of cancer within 12 months of enrollment.

Receipt of chemotherapy, biologic immunomodulators (including JAK inhibitors), or immunosuppressive therapies within 8 weeks of randomization, or receipt of rituximab or other B cell-depleting mAb therapy within 6 months of randomization.

NOTE: Other protocol defined inclusion/exclusion criteria apply.

Example 7: Safety and Efficacy of VIB7734 for the Treatment and Prevention of Acute Lung Injury (ALI) in Patients with SARS CoV-2 Infection: Endpoints The primary objective is to assess the potential benefit of VIB7734 for the treatment and prevention of immune-mediated ALI related to SARS-CoV-2 infection in hospitalized patients. The secondary objectives are to evaluate the safety of VIB7734 in this patient population, and to assess the efficacy by other measures in support of the primary endpoint. The exploratory objective is to assess the effect of VIB7734 on selected inflammatory biomarkers, lymphocyte counts, and supportive measures of safety and efficacy, and to assess the PK, PD, and immunogenicity of VIB7734 in this population.

The primary endpoint is the proportion of patients who achieved treatment success through Day 28, defined as avoidance of death and critical illness. Following are the primary outcome measures:

1. Number and proportion of participants who avoid endotracheal intubation or mechanical ventilation. Defined as measure of respiratory failure. [Time Frame: Day 1 (Baseline) through Day 28].
2. Number and proportion of participants who avoid non-invasive positive pressure ventilation (new or increased from pre-COVID diagnosis baseline in patients with obstructive sleep apnea). Defined as measure of respiratory failure. [Time Frame: Day 1 (Baseline) through Day 28].
3. Number and proportion of participants who avoid extracorporeal membrane oxygenation. Defined as measure of respiratory failure. [Time Frame: Day 1 (Baseline) through Day 28].
4. Number and proportion of participants who avoid shock. Defined as systolic blood pressure <90 mm Hg, or diastolic blood pressure <60 mm Hg, or requiring vasopressors. [Time Frame: Day 1 (Baseline) through Day 28].
5. Number and proportion of subjects who avoid a clinical diagnosis of respiratory failure. [Time Frame: Day 1 (Baseline) through Day 28].
6. Multi-organ dysfunction/failure The secondary objectives are to evaluate the safety of VIB7734 in this patient population, and to assess efficacy by other measures in support of the primary endpoint.

Following are the safety outcome measures:
1. Number of Participants with Treatment-emergent Adverse Events (TEAEs), Treatment-emergent fatal and life-threatening SAEs, Treatment-emergent Serious Adverse Events (TESAEs). Defined as measure of safety. [Time Frame: Day 1 (Baseline) through Day 70].
2. Change in safety laboratory parameters. Safety evaluation via review of labs (white blood cell (WBC) with differential counts, hemoglobin, platelet count, liver function tests (aspartate aminotransferase [AST], alanine aminotransferase [ALT], and total bilirubin levels), serum chemistry, cardiac troponin coagulation markers (prothrombin time [PT], partial thromboplastin time [PTT], D dimer, fibrinogen), and urinalysis). [Time Frame: Day 1 (Baseline) through Day 70].

Following are the exploratory endpoints:
1. Change from baseline in lymphocyte count and inflammatory markers including, but not limited to, high sensitivity C-reactive protein (hsCRP), ferritin, lactate dehydrogenase (LDH), and complement C3/C4.
2. Blood pDC counts.
3. Serum concentrations of VIB7734.
4. Anti-drug antibody responses (ADAs) to VIB7734.
5. Change from baseline in selected biomarkers relevant for hyperinflammation.
6. Initiation or intensification of antiviral therapy in response to worsening of patient condition.

---

What is claimed is:

1. A method for treating or preventing immune-mediated pulmonary injury (IMPI) in a subject infected with a respiratory virus, the method comprising administering to the subject an anti-immunoglobulin-like transcript 7 (ILT7) antibody, thereby treating or preventing the IMPI, wherein the anti-ILT7 antibody comprises the heavy chain variable region (VH) of SEQ ID NO: 1 and the light chain variable region (VL) of SEQ ID NO:2.

2. The method of claim 1, wherein the respiratory virus is selected from the group consisting of rhinovirus, adenovirus, influenza virus, respiratory syncytial virus, enterovirus D68, Severe Acute Respiratory Syndrome-coronavirus (SARS-CoV), Middle Eastern Respiratory Syndrome-coronavirus (MERS-COV), and Severe Acute Respiratory Syndrome-coronavirus-2 (SARS-COV-2).

3. The method of claim 2, wherein the respiratory virus is SARS-CoV-2.

4. The method of claim 3, wherein the subject is a high-risk subject.

5. The method of claim 4, wherein the high-risk subject is a subject that is at least 60 years old, has a pre-existing respiratory condition or is immunocompromised.

6. The method of claim 1, wherein the respiratory virus is a coronavirus.

7. The method of claim 6, wherein, prior to the administering, the subject exhibited at least one symptom selected from the group consisting of: increased circulating levels of pro-inflammatory cytokines, increased local levels of pro-inflammatory cytokines, T-cell lymphopenia, and increased inflammatory markers.

8. The method of claim 1, wherein, prior to the administration, the subject exhibited at least one clinical marker of IMPI selected from the group consisting of: shortness of breath, hypoxia, abnormal chest imaging, and transaminitis.

9. The method of claim 1, wherein the anti-ILT7 antibody is daxdilimab.

10. The method of claim 9, wherein the administration reduces levels of circulating plasmacytoid dendritic cells (pDCs).

11. The method of claim 10, wherein the reduction of circulating pDCs is sustained for at least 15 days.

12. The method of claim 1, wherein the anti-ILT7 antibody is afucosylated.

13. The method of claim 1, wherein the anti-ILT7 antibody is administered at a dose of about 0.1 mg to about 1000 mg.

14. The method of claim 13, wherein the anti-ILT7 antibody is administered at a dose of about 5 mg to about 150 mg.

15. The method of claim 1, wherein the anti-ILT7 antibody is administered by subcutaneous injection.

16. The method of claim 1, further comprising administering a second therapy.

17. The method of claim 16, wherein the second therapy is selected from the group consisting of: remdesivir, a corticosteroid, an interleukin-6 (IL-6) inhibitor, an interleukin-2 (IL-2) inhibitor, a plasma transfusion, and a janus kinase (JAK) inhibitor.

18. A method for treating or preventing immune-mediated pulmonary injury (IMPI) in a subject infected with a respiratory virus, the method comprising administering an anti-immunoglobulin-like transcript 7 (ILT7) monoclonal antibody, thereby treating or preventing the IMPI, wherein the anti-ILT7 antibody comprises the heavy chain variable region (VH) of SEQ ID NO: 1 and the light chain variable region (VL) of SEQ ID NO:2.

19. The method of claim 18, wherein the respiratory virus is selected from the group consisting of rhinovirus, adenovirus, influenza virus, respiratory syncytial virus, enterovirus D68, Severe Acute Respiratory Syndrome-coronavirus (SARS-COV), Middle Eastern Respiratory Syndrome-coronavirus (MERS-COV), and Severe Acute Respiratory Syndrome-coronavirus-2 (SARS-COV-2).

20. The method of claim 18, wherein the subject is at high risk.

21. The method of claim 20, wherein the respiratory virus is Severe Acute Respiratory Syndrome-coronavirus-2 (SARS-COV-2).

22. The method of claim 18, wherein the anti-ILT7 antibody is administered at a dose of about 0.1 mg to about 1000 mg.

23. The method of claim 22, wherein the anti-ILT7 antibody is administered at a dose of about 5 mg to about 150 mg.

24. The method of claim 23, wherein the anti-ILT7 antibody is administered at a dose of about 150 mg.

25. The method of claim 18, wherein the anti-ILT7 antibody is administered by subcutaneous injection.

26. A method for treating a subject infected with a coronavirus, the method comprising administering an anti-immunoglobulin-like transcript 7 (ILT7) antibody, thereby treating the coronavirus infection or a symptom thereof, wherein the anti-ILT7 antibody comprises the heavy chain variable region (VH) of SEQ ID NO: 1 and the light chain variable region (VL) of SEQ ID NO:2.

27. The method of claim 26, wherein the symptom is treated, and wherein the symptom is selected from the group consisting of: increased levels of a pro-inflammatory cytokine, T-cell lymphopenia, and increased levels of an inflammatory marker.

* * * * *